United States Patent
Yamamichi et al.

(10) Patent No.: US 7,915,053 B2
(45) Date of Patent: Mar. 29, 2011

(54) SUBSTRATE FOR TARGET SUBSTANCE DETECTING DEVICE, TARGET SUBSTANCE DETECTING DEVICE, TARGET SUBSTANCE DETECTING APPARATUS AND METHOD USING THE SAME, AND KIT THEREFOR

(75) Inventors: Junta Yamamichi, Cambridge, MA (US); Satoru Nishiuma, Kawasaki (JP); Tomohiro Yamada, Yokohama (JP); Masaya Ogino, Kawasaki (JP); Ryo Kuroda, Kawasaki (JP); Hidenori Shiotsuka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 404 days.

(21) Appl. No.: 12/088,023

(22) PCT Filed: Dec. 20, 2006

(86) PCT No.: PCT/JP2006/325994
§ 371 (c)(1),
(2), (4) Date: Mar. 25, 2008

(87) PCT Pub. No.: WO2007/072986
PCT Pub. Date: Jun. 28, 2007

(65) Prior Publication Data
US 2009/0117669 A1 May 7, 2009

(30) Foreign Application Priority Data

Dec. 22, 2005 (JP) ................................. 2005-370757

(51) Int. Cl.
*G01N 33/551* (2006.01)
(52) U.S. Cl. .................. 436/524; 422/82.11; 435/287.2; 435/288.7; 436/164; 436/525; 436/805

(58) Field of Classification Search .................. None
See application file for complete search history.

(56) References Cited

U.S. PATENT DOCUMENTS

| | | | | |
|---|---|---|---|---|
| 4,444,879 A | * | 4/1984 | Foster et al. | 435/7.95 |
| 5,415,842 A | * | 5/1995 | Maule | 422/82.05 |
| 5,478,755 A | * | 12/1995 | Attridge et al. | 436/518 |
| 7,332,329 B2 | | 2/2008 | Wark et al. | |

(Continued)

FOREIGN PATENT DOCUMENTS

JP 2000-356587 A 12/2000

(Continued)

OTHER PUBLICATIONS

Hackh's Chemical Dictionary, 4th Edition, 1969, p. 720.*

(Continued)

*Primary Examiner* — Christopher L Chin
(74) *Attorney, Agent, or Firm* — Fitzpatrick, Cella, Harper & Scinto

(57) ABSTRACT

A substrate for forming a target substance detecting device includes a supporting member, an underlying layer disposed on a surface of the supporting member, and a metal pattern layer, disposed on a surface of the underlying layer, for being bound to a target substance trapping substance capable of trapping a target substance in a specimen solution at least containing water as a liquid medium to detect the target substance by utilizing plasmon resonance. The underlying layer has a refractive index $n_b$ satisfying the following relationship:

$$0.90\, n_a \leq n_b \leq 1.05\, n_a,$$

wherein $n_a$ represents a refractive index of water.

16 Claims, 16 Drawing Sheets

U.S. PATENT DOCUMENTS

| | | | |
|---|---|---|---|
| 7,387,901 | B2 | 6/2008 | Nishiuma et al. |
| 7,399,445 | B2 | 7/2008 | Kuroda et al. |
| 2006/0115861 | A1 | 6/2006 | Shiotsuka et al. |
| 2006/0170918 | A1 | 8/2006 | Nishiuma |
| 2006/0275811 | A1 | 12/2006 | Hatakeyama et al. |
| 2007/0153412 | A1 | 7/2007 | Takeda et al. |
| 2007/0178522 | A1 | 8/2007 | Shiotsuka et al. |
| 2007/0285666 | A1 | 12/2007 | Utsunomiya et al. |
| 2008/0108132 | A1 | 5/2008 | Ban et al. |

FOREIGN PATENT DOCUMENTS

| | | |
|---|---|---|
| JP | 2003-270132 A | 9/2003 |
| JP | 3452837 B2 | 10/2003 |
| JP | 2005-312446 A | 11/2005 |
| WO | 01/69209 A1 | 9/2001 |

OTHER PUBLICATIONS

Xu, et al., "Surface plasmon resonance of sputtered Ag films: substrate and mass thickness dependence", Appl. Phys. A, vol. 80, 2005, pp. 1535-1540.

Notification of Transmittal of the International Search Report and the Written Opinion, PCT/JP2006/325994, dated Mar. 22, 2007.

U.S. Appl. No. 10/548,442, filed Mar. 14, 2008; Applicants: Hidenori Shiotsuka, et al.

U.S. Appl. No. 11/913,047, filed May 29, 2006: Applicants: Hidenori Shiotsuka, et al.

U.S. Appl. No. 11/913,045, filed Mar. 30, 2006: Applicants: Hidenori Shiotsuka, et al.

U.S. Appl. No. 11/916,254, filed Nov. 30, 2007: Applicants: Hidenori Shiotsuka, et al.

U.S. Appl. No. 11/995,911, filed Sep. 1, 2006: Applicants: Takeshi Imamura, et al.

U.S. Appl. No. 11/869,711, filed Oct. 9, 2007: Applicants: Satoru Hatakeyama, et al.

Tam, et al. "Geometrical Parameters Controlling Sensitivity of Nanoshell Plasmon Resonances to Changes in Dielectric Environment", J. Phys. Chem. B. 2004, 17290-17294.

\* cited by examiner (A)

(B)

(C)

(A)

(B)

(C)

(D)

(E)

(F)

(G)

(A)

(B)

(C)

(A)

(B)

(C)

(A)  (B)

SUBSTRATE FOR TARGET SUBSTANCE DETECTING DEVICE, TARGET SUBSTANCE DETECTING DEVICE, TARGET SUBSTANCE DETECTING APPARATUS AND METHOD USING THE SAME, AND KIT THEREFOR

TECHNICAL FIELD

The present invention relates to a target substance detecting device, a substrate therefor, a target substance detecting apparatus, a detecting method, and a detection kit, which are useful for detecting presence of a target substance in a specimen solution.

BACKGROUND ART

As a type of sensors, a biosensor has been known. The biosensor is a measuring device utilizing an excellent biomolecular recognition ability of a living body (organism) or biomolecule and recently expected to be widely applied to various fields including not only a medical field but also an environmental field, a foodstuff field, etc.

Generally, the biosensor is constituted by a trapping substance for recognizing and trapping a substance to be subjected to measurement (hereinafter referred to as a "target substance") and a detecting device for detecting a physical/chemical change caused during the recognition and trapping of the target substance and converting the change into a detectable signal such as an electric signal or an optical signal. In the living body, as a combination of substances having a mutual affinity, there are combinations of, e.g., enzyme-substrate, antigen-antibody, and DNA-DNA. The biosensor utilizes such a principle that one of the substances of the combination is fixed or carried on a supporting member to be used as a component of the trapping substance and thus the other substance is selectively measurable. Further, as the detecting device, there have been proposed detecting devices of various types including an oxygen electrode, a hydrogen peroxide electrode, an ion electrode, an ion-sensitive field-effect transistor (ISFET), a thermistor, etc. In recent years, a quartz resonator, a surface-acoustic-wave (SAW) device, a plasmon resonator, and the like are used in some cases.

Of the various sensors, a sensor including a detection system utilizing plasmon resonance has the following advantages (1) and (2):

(1) it is possible to simply constitute an assay since there is no need to use a labeled molecule such as a fluorescent dye, and (2) it is possible to directly effect real-time monitoring of a process of adsorption reaction onto surfaces of metal fine particles.

Therefore, such a measuring method is expected to be applied to various assays.

In the measuring method, detection of a substance present in the neighborhood of metal fine particles is effected utilizing such a phenomenon that a characteristic resonance spectrum appears by localized plasmon resonance induced when metal fine particles of gold, silver, or the like are fixed on a surface of a substrate and light is incident on the metal fine particles. It has been known that a waveform of the resonance varies depending on a dielectronic constant of a medium present in the neighborhood of the metal fine particles.

An absorbance at a resonance peak becomes larger as the dielectric constant of the medium becomes larger, and shifts toward a long wavelength.

For example, Japanese Patent No. 3452837 has proposed a system using a gold colloid with about 20 nm of diameter is proposed. In the system, a refractive index of a medium located with a distance corresponding to an approximately diameter of metal fine particles fixed on a substrate is detected, so that it is possible to detect adsorption or deposition of a substance on the surfaces of the metal fine particles.

On the other hand, as proposed by Felicia Tam et al. (J. Phys. Chem. B., 2004, Vol. 108, No. 45, pp. 17290-17294), there is an example of device structure which aims at enhancement of detection capability by producing core shell type fine particles that are made by coating gold thin films on dielectric cores.

Further, Japanese Laid-Open Patent Application No. 2003-270132 has disclosed a sensor apparatus which includes a metal film provided with a plurality of openings to which a sensor material is fixed, a light source, and a light detector for detecting transmitted light or reflected light from the openings. In the sensor apparatus, the openings are periodically arranged in a first in-plane direction of the metal film.

However, when an affinity assay such as an immunoassay utilizing specify of an antigen-antibody reaction is effected by using a conventional device for detecting a target substance through utilization of the plasmon resonance, a sufficient detection sensitivity cannot be obtained in some cases. This problem regarding the detection sensitivity is one of problems to be solved in the case of applying a detecting method utilizing the plasmon resonance to the affinity assay in place of existing fluorescent immunoassay or chemiluminescent immunoassay. Accordingly, the problem regarding the detection sensitivity is a major problem for increasing use of a measuring method utilizing the localized plasmon resonance.

DISCLOSURE OF THE INVENTION

The present invention has accomplished in view of the above-described problem, and a principal object thereof is to provide a target substance detecting device capable of improving detection sensitivity in detection of a target substance by utilizing localized plasmon resonance and to also provide a substrate for preparing the target substance detecting device.

Another object of the present invention is to provide a target substance detecting apparatus and target substance detecting method which employ the target substance detecting device.

A further object of the present invention is to provide a kit for the target substance detecting method.

According to an aspect of the present invention, there is provided a substrate for forming a target substance detecting device, comprising:

a supporting member;

an underlying layer disposed on a surface of the supporting member; and a metal pattern layer, disposed on a surface of the underlying layer, for being bound to a target substance trapping substance capable of trapping a target substance in a specimen solution at least containing water as a liquid medium to detect the target substance by utilizing plasmon resonance, wherein the underlying layer has a refractive index $n_b$ satisfying the following relationship:

$$0.90\, n_a \leq n_b \leq 1.05\, n_a,$$

wherein $n_a$ represents a refractive index of water.

According to another aspect of the present invention, there is provided a target substance comprising:

the substrate described above; and a target substance trapping substance, wherein the metal pattern layer of the substrate is bound to the target substance trapping substance.

According to another aspect of the present invention, there is provided a target substance detecting apparatus for detecting a target substance in a specimen solution, comprising:

the target substance detecting device described above;

specimen solution supplying means for supplying the specimen solution to the target substance detecting device; and detecting means for detecting trapping of the target substance by the target substance trapping substance of the target substance detecting device.

According to a further aspect of the present invention, there is provided a target substance detecting method for detecting presence or absence of a target substance in a specimen solution at least containing water as a liquid medium or for detecting an amount of the target substance, comprising the steps of:

bringing the target substance detecting device described above into contact with the target substance; and detecting trapping the target substance on the target substance detecting device when the specimen solution contains the target substance.

According to a still further aspect of the present invention, there is provided a target substance detection kit for detecting presence or absence of a target substance in a specimen solution or an amount of the target substance, comprising:

the target substance detecting device described above; and a reagent necessary for trapping of the target substance by the target substance detecting device.

These and other objects, features, and advantages of the present invention will become more apparent upon consideration of the following description of the preferred embodiments of the present invention, taken in conjunction with the accompanying drawings.

BEST MODE FOR CARRYING OUT THE INVENTION

In the target substance detecting device according to the present invention, a metal pattern layer to be disposed on a supporting member is disposed on a surface of a light-transmissive (transparent) underlying having a refractive index (nb) which is equal or close to a refractive index of water in an environment (such as a temperature or a pressure) in which measurement is effected. More specifically, the refractive index (nb) of the underlying satisfies the following relationship:

$$0.90\, na \leq nb \leq 1.05\, na,$$

wherein na represents a refractive index of water.

The refractive index (na) (at an interface with air phase) is 1.34 at a wavelength of 589 nm.

Therefore, by selecting the refractive index (at an interface with air phase) of the underlying layer under the same condition from a range of 1.20-1.40, it is possible to achieve an effect of the present invention. Further, the refractive index of the underlying layer may preferably be selected from a range of 1.30-1.36.

Hereinbelow, the target substance detecting device, a detecting apparatus and a detecting method using the target substance detecting device, and a kit for the detecting method according to the present invention will be described in detail.

(Substrate for Target Substance Detecting Device)

A substrate for preparing the target substance detecting device is constituted by the supporting member, the underlying layer which has the refractive index equal or close to that of water and is disposed on the supporting member, and the metal pattern layer disposed on the underlying layer. A shape (planar shape) or structure of the metal pattern layer can be appropriately selected depending on the type of a detection system. In the case of applying the metal pattern layer to a detecting system utilizing plasma resonance, a constitution in which the metal pattern layer is disposed on the underlying layer (on the supporting member) as an isolated (independent) layer or a constitution which the metal pattern layer disposed on the underlying layer (on the supporting member) is provided with openings (holes).

Hereinbelow, preferred embodiments of these constitutions will be described.

(1) Isolation Type Metal Pattern Layer

Figure 1:
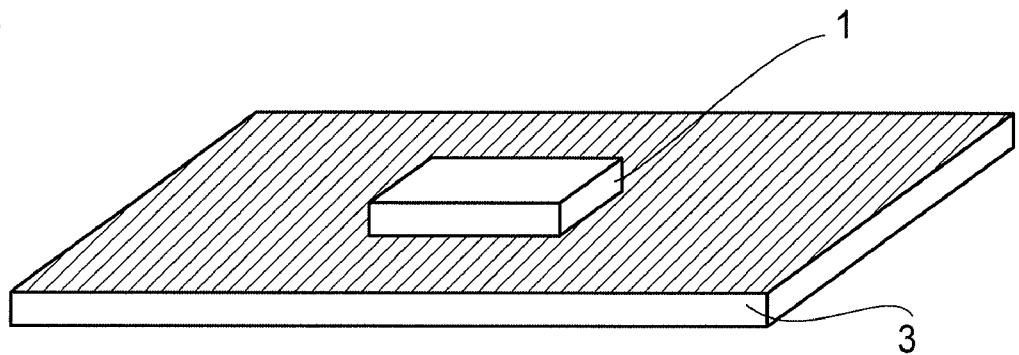
FIGS. 1(A), 1(B) and 1(C) are schematic views each for illustrating a metal structure in an embodiment of the present invention.
Figure 1:
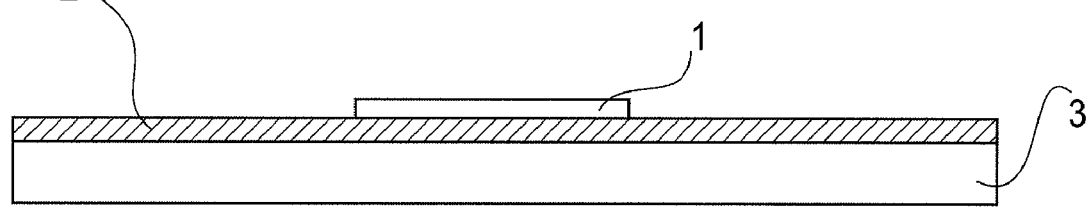
Figure 1:
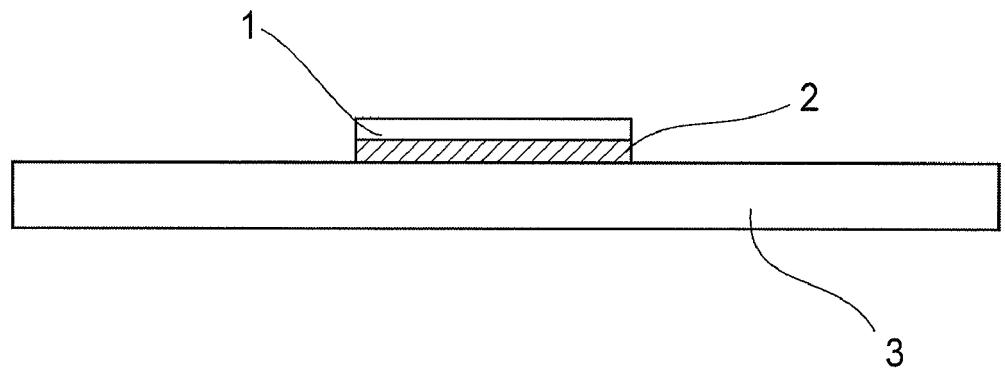
Figure 2:
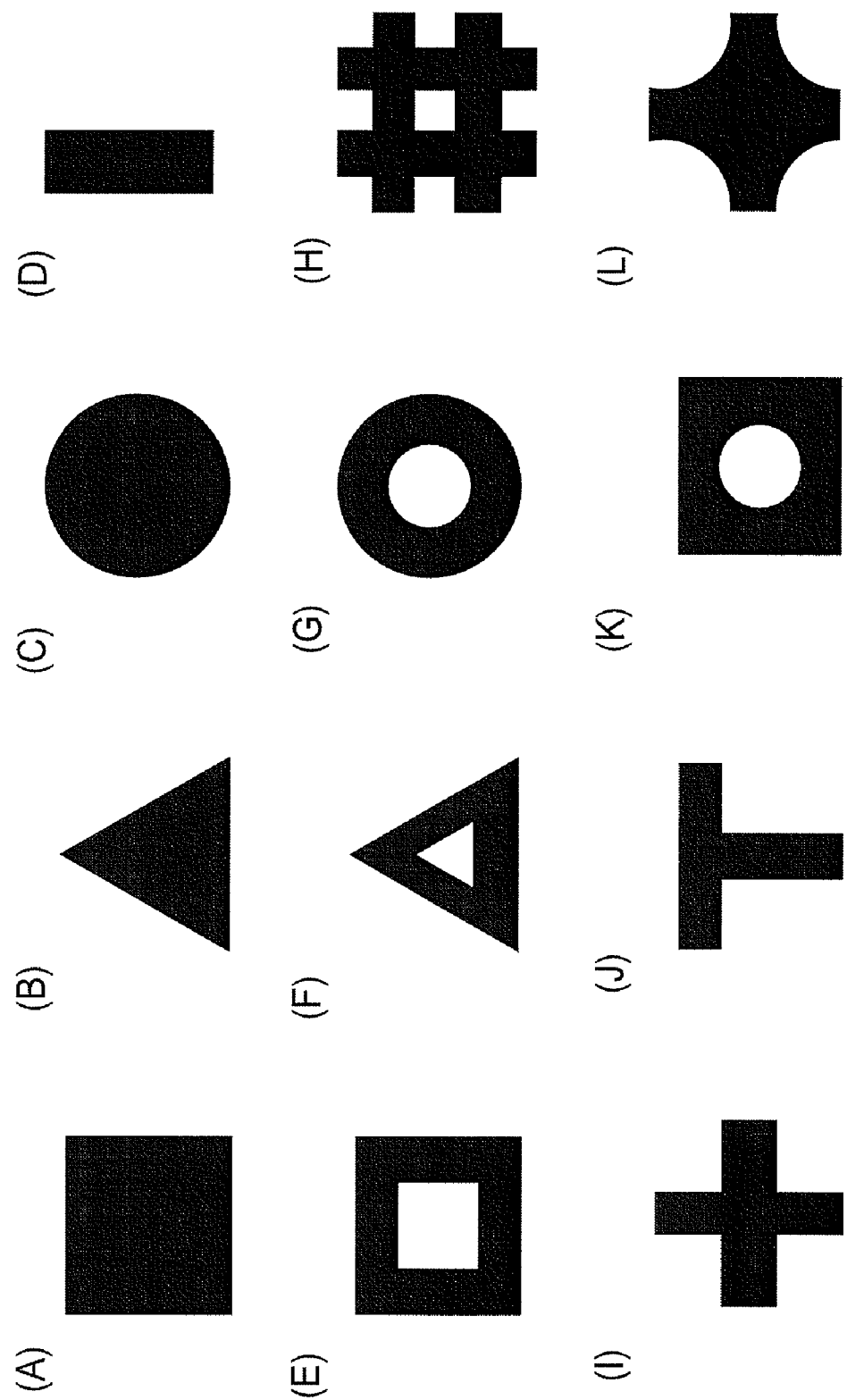
FIGS. 2(A) to 2(L) are schematic views each for illustrating a planar shape of the metal structure in an embodiment of the present invention.

FIGS. 1(A) to 1(C) show an example of a substrate for a target substance detecting device including a metal pattern layer 1 having a rectangular planar shape. Referring to these figures, the substrate for the target substance has such a structure that an isolated metal pattern layer (metal structure) 1 is disposed on a surface of an underlying layer 2 which is disposed on a surface of a supporting member 3. The underlying layer 2 has a refractive index equal or close to that of water. FIG. 1(A) is a perspective view of the substrate at the substrate surface, and FIGS. 1(B) and 1(C) are sectional views of the surface in a direction perpendicular to the substrate. The underlying layer 2 may also be patterned similarly as in the metal pattern layer 1 as shown in FIG. 1(C). However, the structure of the substrate shown in FIGS. 1(A) and 1(B) are a simplest structural example. Further, the metal pattern layer 1 may have two-dimensional (planar) shapes as shown in FIGS. 2(A) to 2(L). For example, in view of a production process, the metal pattern layer may have a shape including inner and outer portions having different contours different in shape as shown in FIG. 2(K) and a cross-like shape with rounded portions, not right-angle corners, at an intersection portion as shown in FIG. 2(L).

The metal pattern layer may be formed of any one of metals, such as gold, silver, copper, aluminum, and platinum, preferably noble metals, and alloys of these metals. These materials may preferably be selected from the viewpoint of adhesiveness to the underlying layer. In the case where the underlying layer is formed of a fluorine-containing material, it is also possible to form a thin layer of chromium or titanium between the underlying layer and the metal pattern layer.

A size of dimension of the planar shape of the metal pattern layer, i.e., a distance from one point to another point at an outer peripheral portion of the planar shape may preferably be in a range of 10-1450 nm, more preferably 50-450 nm. The distance in this case is a maximum distance between any two points. For example, in the case of parallel cross-like pattern with a width W shown in FIG. 13(A), a distance between points X and Y is a maximum, so that this distance is taken as the maximum distance to be within the above described range. Similarly, also in the case of a rectangular frame-like pattern with a width W shown in FIG. 13(B), a distance of a diagonal line L between points X and Y a maximum, so that the diagonal line L is taken as the maximum distance. In the case of a circular ring pattern shown in FIG. 2(G), a diameter of an outer circle is taken as the maximum to be within the above described range. When the maximum distance of the planar shape of the metal pattern layer 1 is within the above described range, it is possible to further effectively obtain localized plasmon resonance capable of achieving a target detection sensitivity.

In the case where the metal pattern layer 1 has the planar shape including a belt-like portion, e.g., as shown in FIGS. 2(E) to 2(L), a width of the belt-like portion (hereinafter referred to as a "belt width") is not particularly limited so long as the localized plasmon resonance, which is intended to be obtained by the present invention, is obtained. The belt width may preferably be in a range of 10-100 nm.

Figure 13:
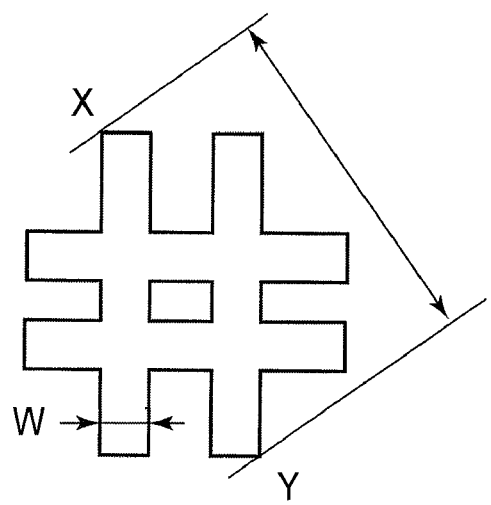
FIGS. 13(A) and 13(B) are schematic views each for illustrating a size of a metal pattern.
Figure 13:
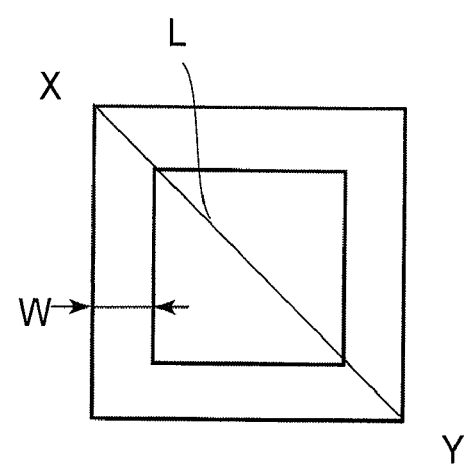

The belt width is a difference between radii of an outer peripheral circle and an inner peripheral circle, for example, in the case of a circular ring pattern in FIG. 2(G), or is the width W shown in FIGS. 13(A) and 13(B), respectively in the case of the parallel cross-like pattern and the rectangular frame-like pattern.

Figure 3:
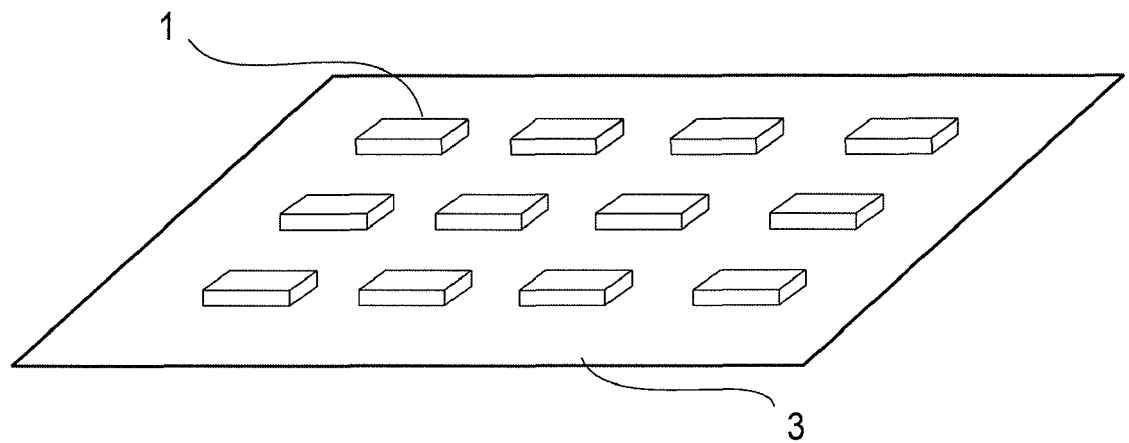
FIG. 3 is a schematic view for illustrating a detecting device in an embodiment of the present invention.

One or a plurality of the metal pattern layers are provided on the underlying layer according to necessity. An interval (d) between adjacent metal pattern layers in the case of the plurality of ones can be selected from a range satisfying the following relationship:

$$(\lambda max-50\ nm) \leq d \leq (\lambda max+50\ nm),$$

wherein $\lambda max$ represents a maximum absorption wave length when a single metal pattern layer is disposed on the underlying layer (on the supporting member). More specifically, the interval (d) may preferably be in a range of is 50-2000 nm, or more preferably 400-1500 nm. This is because an interaction between the metal pattern layers by the localized plasmon affects spatial distribution and strength of an electric field. As the interval becomes large, a density of the metal pattern layers is lowered to weaken a signal strength, so that a special optical system is required. A plurality of metal pattern layers different in at leas tone of the planar shape and its size can be provided on the underlying layer. In consideration of production efficiency of the metal pattern layers, simple structure of the detection system and the like, as shown in FIG. 3, it is preferable to dispose the metal pattern layers 1 with the same shape and size in an array on the supporting member 3 of several-millimeter square. Such disposition makes measurement of transmitted light, scattered light, or reflected light easy.

A thickness, outer shape, and belt width of the metal pattern layer and the interval between adjacent metal pattern layers affect a peak position of localized plasmon resonance spectrum, so that the metal pattern layers may preferably be formed in a size suitable for measurement. Of the respective planar shapes shown in FIGS. 2(A) to 2(L), those having a loop portion and/or a branch connection are preferable for further improving the detection sensitivity. This may be attributable to the following points (a) to (c) acting in a synergistic manner:

(a) increase in contour length of each metal pattern layer,
(b) increase in the number of corners in the case of utilizing the branch connection, and
(c) decrease in distance between edges of planar shape of the metal pattern layer.

The isolated metal pattern layers (metal structures) as shown in FIG. 1 and FIGS. 2(A) to 2(L) can be formed in a thickness from about 10 nm to about 20 nm.

(2) Opening the Metal Pattern Layer

Figure 15:
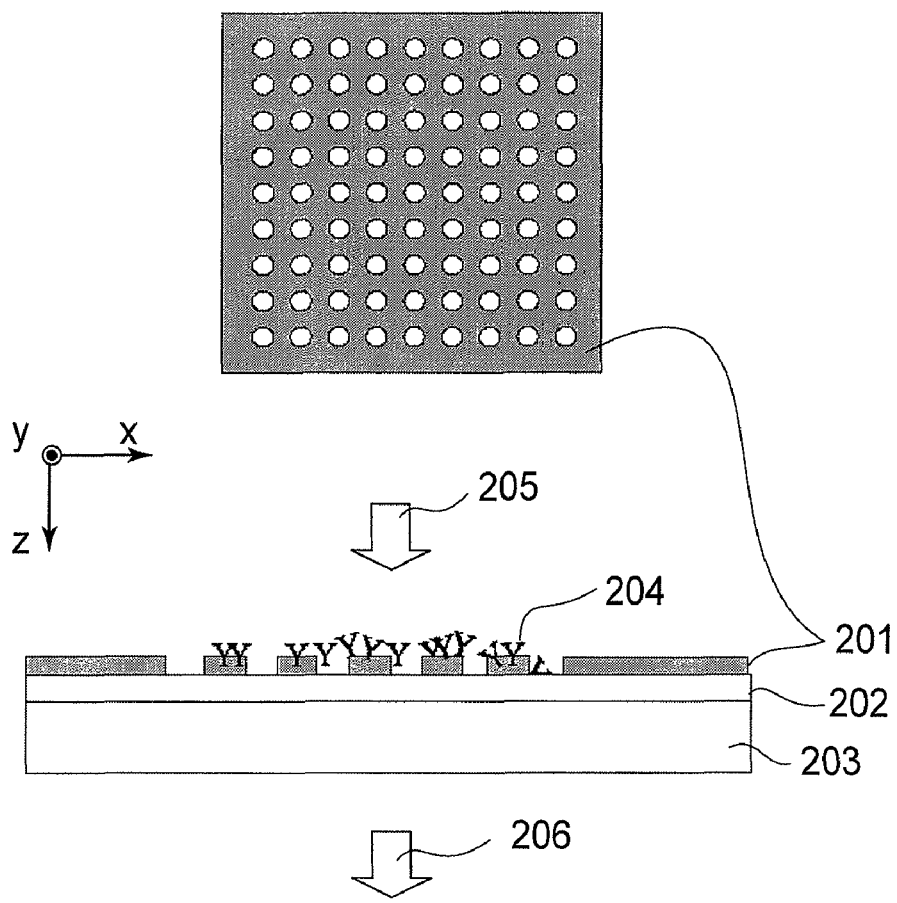
FIGS. 15 and 16 are schematic views each for illustrating an example of a target substance detecting device of the present invention.

An example of a metal pattern layer provided with openings no a surface of an underlying layer is shown in FIG. 15 including a plan view and a sectional view in a direction perpendicular to a substrate. Referring to FIG. 15, a metal pattern layer 201 of this substrate is disposed on a supporting member 203 through an underlying layer 202 disposed between the metal pattern layer 201 and the supporting member 203. The metal pattern layer 201 is provided with a multiplicity of openings regularly arranged with the same circular shape.

Figure 16:
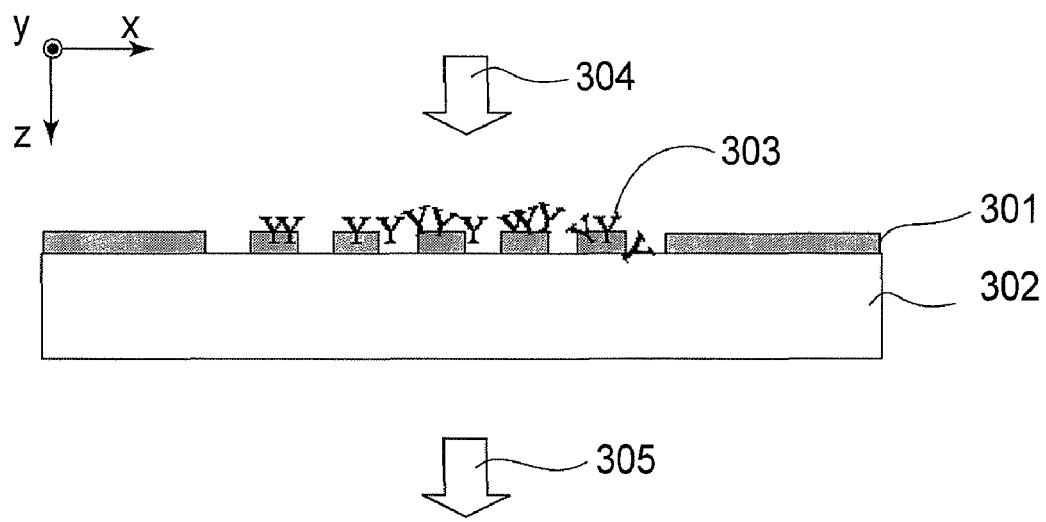

The openings can be formed by removing a part of the metal pattern layer 201 utilizing etching or the like so that the underlying layer 202 is exposed at a bottom of the openings. FIG. 16 shows such a constitution that a refractive index of a supporting member 302 is equal or close to a refractive index of water.

The openings provided to the metal pattern layer can have various planar shapes. Examples of the metal pattern layer having the openings may include a metal thin film 401 having minute slit-like openings in an array as shown in FIG. 17(A), a metal thin film 403 having minute slit-like openings in an array with alternately different (larger and smaller) intervals as shown in FIG. 17(C), a metal thin film 402 having two-dimensionally arranged rectangular openings in an array as shown in FIG. 17(B), and a metal thin film 404 having two-dimensionally arranged triangular openings in an array as shown in FIG. 17(D). When the plurality of openings is provided to the metal pattern layer, openings having different shapes may also be provided to the same metal pattern layer. However, in view of an advantage of production, it is preferable that opening having the same shape are regularly disposed.

Further, in this case, the metal pattern layer may be formed of any one of metals, such as gold, silver, copper, aluminum, and platinum, preferably noble metals, and alloys of these metals. These materials may preferably be selected from the viewpoint of adhesiveness to the underlying layer. In the case where the underlying layer is formed of a fluorine-containing material, it is also possible to form a thin layer of chromium or titanium between the underlying layer and the metal pattern layer.

The metal pattern layer in this case can be formed in a thickness of approximately 10-200 nm and the thickness may be appropriately selected in a wavelength range of irradiation light. For example, in the case of Au, the thickness may preferably be approximately 50 nm. A pattern shape of the metal pattern layer may preferably be such a pattern shape that light interacting with free electrons of metal constitutes a principal component and that the film (layer) is provided with a plurality of openings. The openings may have various cross-sectional shapes such as a circular shape, an elliptical shape, a triangular shape, a rectangular shape, and a polygonal shape.

A distance between adjacent two openings in the case of providing the plurality of openings may preferably be not more than a wavelength of irradiation light and a selected depending on a desired detection system. The distance between the openings can be set similarly as in the case of the distance between the isolated metal pattern layers described above.

(Underlying Layer)

The underlying layer is formed of a material having a refractive index equal or close to that of water as described above. The material includes an inorganic material and an organic material. Examples of the inorganic material may include magnesium fluoride (refractive index: 1.37) and lithium fluoride (refractive index: 1.39). Examples of the organic material may include various polymers.

As the material for forming the underlying layer, it is preferred to use a fluorine-containing material. As an organic material containing fluorine, a fluorine-containing resin is preferable.

Further, from the viewpoint of optical characteristics such as transparency and refractive index, a fluorine-containing resin having an amorphous structure (e.g., polytetrafluoroethylene (PTFE); refractive index: 1.35) may more preferably be used. Specific examples of such a fluorine-containing resin may include "CYTOP" (mfd. By ASAHI GLASS Co., Ltd.), "Teflon AF" (mfd. By DuPont), and a mixture thereof.

In the present invention, the metal pattern layer includes the underlying layer which has the refractive index equal or close to that (1.34) of water containing the target substance, so that the metal pattern layer is placed in a state in which it is surrounded by the material having the refractive index equal or close to that of water. As a result, reflection from a (dielectric) layer having a different refractive index is suppressed, so that disturbance of the plasmon resonance is suppressed, thus resulting in a sharp plasmon resonance peak.

A thickness of the underlying layer can appropriately be selected depending on a type thereof such as the case where it also functions as a supporting member. In the case where the underlying layer is provided no a separately prepared supporting member (e.g., the case of type (II) of the supporting member described below), the thickness of the underlying layer may preferably be 10 nm or more and 50 μm or less, more preferably 100 nm or more and 30 μm or less.

The present invention of the underlying layer may generally be determined by a method of obtaining a refractive index from a spectral reflectance and transmittance by means of a microspectrophotometric apparatus and a method according to ellipsometry.

(Supporting Member)

The supporting member on which the underlying layer and the metal pattern layer are provided may be such a member that it can support these layers and permit detection of the target substance by using these layers. Further, the supporting member itself may also function as the underlying layer. On the supporting member, a plurality of layers including a topmost underlying layer may also be formed. Examples of the type of the supporting member may include the following two types:

(I) the supporting member is constituted by a single layer having also a function as the underlying layer, and (II) the supporting member has the underlying layer thereon.

In the type (II) of the supporting member, an optically transparent glass plate, a quartz plate, and resin plates of polycarbonate, polyethylene, and the like are usable as the supporting member. Further, as the supporting member having also the function as the underlying layer in the type (I), a plate of a fluorine-containing resin having a refractive index equal or close to that of water may suitably be used.

(Preparation Method of Substrate)

(i) Isolated Metal Pattern Layer

An example of a method of forming the isolated metal pattern layer will be described with reference to the drawings.

Figure 5:
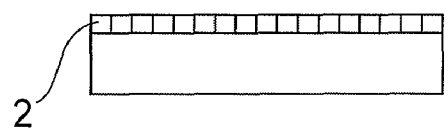
FIGS. 5(A) to 5(G), FIGS. 6(A) to 6(C), and FIGS. 7(A) to 7(C) are schematic views for illustrating production processes of detecting devices in embodiments of the present invention.
Figure 5:
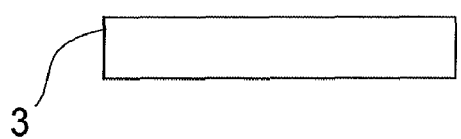
Figure 5:
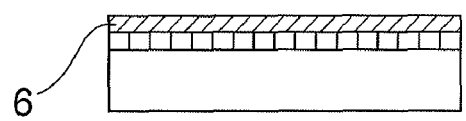
Figure 5:
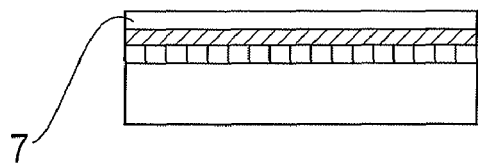
Figure 5:
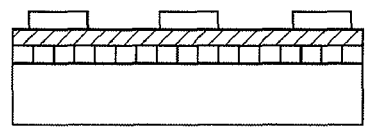
Figure 5:
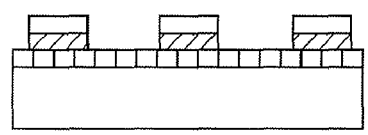
Figure 5:
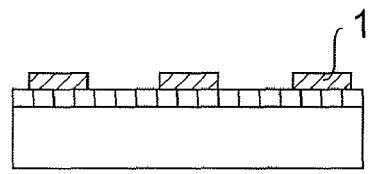

First, on a substrate 3 (FIG. 5(A)), an underlying layer 2 is formed using a material for forming the underlying layer (FIG. 5(B)). In the case of using a resin material or the like, a spin coat method is used. Further, in the case of using an inorganic material, a (vacuum) deposition method can be utilized.

Next, a metal thin film 6 is formed by a sputtering method or a (vacuum) deposition method on the underlying layer 2 (FIG. 5(C)). An electron beam resist 7 is formed by spin coating thereon (FIG. 5(D)), exposure is performed by an electron beam lithographic system, and an after-development resist pattern is obtained (FIG. 5(E)). Then, an unnecessary metal thin film is etched (FIG. 5(F)), and the resist is removed to form an array-like metal pattern layer 1 under which the underlying layer 2 formed of a fluorine-containing material is disposed (FIG. 5(G)).

For patterning, it is possible to use a focused ion beam processing device, an X-ray exposure device, and an EUV exposure device in addition to the electron beam lithographic system.

Figure 6:
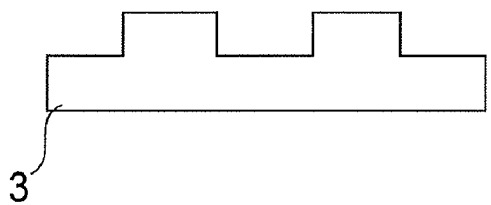
Figure 6:
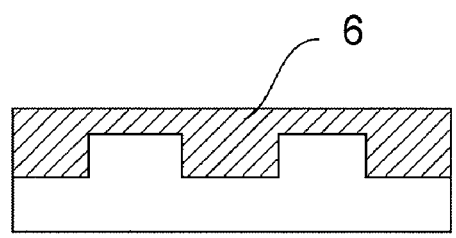
Figure 6:
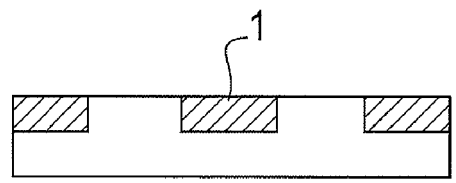

As shown in FIGS. 6A to 6C, a production method using a supporting member (FIG. 6(A)), having minute projections and recesses, produced by a mold method using a fluorine-containing resin material is also possible. A metal thin film is formed on a supporting member 3 at the surface having the projections and recesses by the sputtering method or vacuum deposition method (FIG. 6(B)). Next, the surface metal thin film is ground to form a metal structure, which has a desired layer structure, on the supporting member (FIG. 6(C)).

Figure 7:
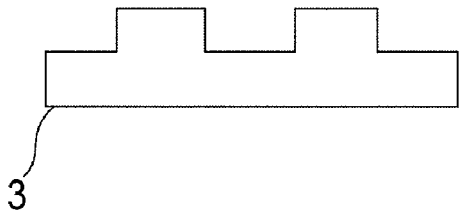
Figure 7:
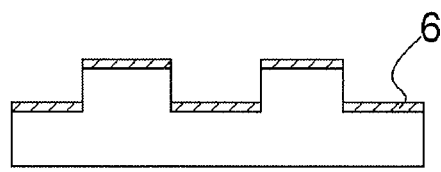
Figure 7:
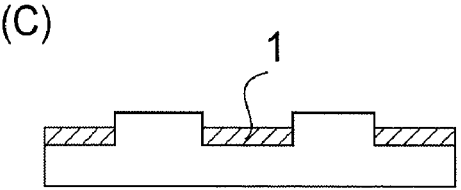

FIGS. 7(A) to 7(C) show a production method when the thickness of the metal pattern layer is smaller than a height (depth) of the projections and recesses of the supporting member. In this case, the projections of the supporting member may be located above the metal pattern layer or a metal thin film may be formed on a wall surface of the projections and recesses. The metal thin film can be also removed using etch back by dry etching instead of grinding.

(ii) Opening-Type Metal Pattern Layer

The opening-type metal pattern layer can be prepared basically in the same manner as the case of the isolated metal pattern layer.

More specifically, as shown in FIGS. 5(A) to 5(G), the underlying layer, the metal thin film, and the resist layer are formed in this order on the supporting member, and a portion of the resist layer corresponding to openings is removed. Then, a resist pattern is formed and the metal thin film is etched through the resist pattern, thus obtaining an opening-type metal pattern layer.

(Target Substance Detecting Device and Target Substance)

Figure 4:
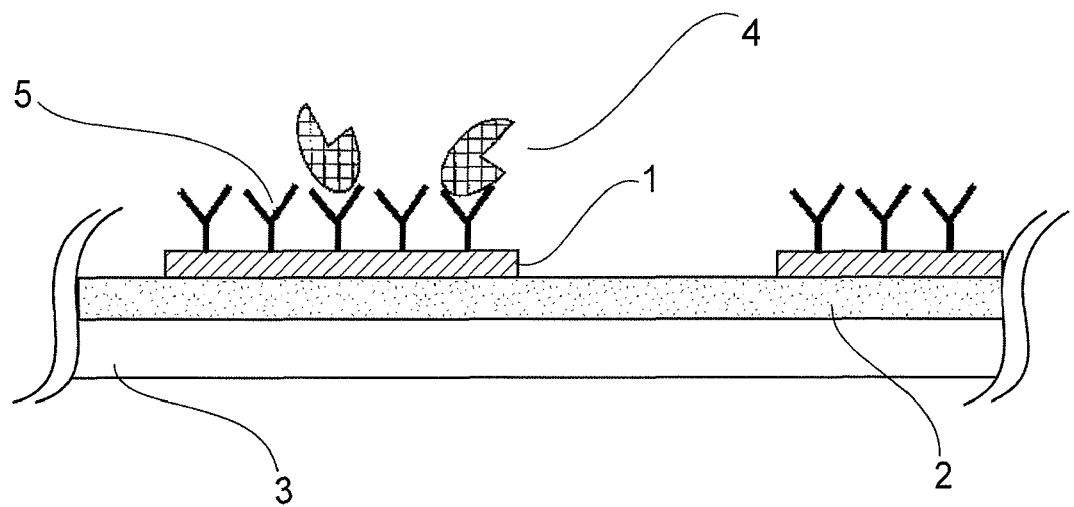
FIG. 4 is a schematic view for illustrating an Example of a trapping substance on a detecting device in an embodiment of the present invention.

It is possible to prepare a target substance detecting device by binding a target substance trapping substance to a metal pattern layer for a substrate capable of having the above described various constitutions. A state in which the target substance trapping substance is fixed on the metal pattern layer is shown in FIGS. 4 and 15.

The target substance is not particularly limited so long as it forms a specific binding pair with the target substance trapping substance. More specifically, the target substance contained in a specimen solution is roughly classified into biomaterials and non-biomaterials. Examples of non-biomaterials of great industrial utility value may include environmental pollutants such as PCBs (polychlorinated biphenyls) different in number/position of chlorine substitutions and dioxins different in number/position of chlorine substitutions, and endocrine disrupters such as so-called environmental hormones.

Examples of the biomaterials may include nucleic acid, protein, sugar chain, lipid, and their complexes. In some cases, the biomaterials contain biomolecule selected from the group consisting of nucleic acid, protein, sugar chain, and lipid. Specific examples of the biomaterials may include DNA, RNA, aptamer, gene, chromosome, cell membrane, virus, antigen, antibody, lectin, hepten, hormone, receptor enzyme, peptide, sphingoglycolipid, and sphingolipid. Further, bacteria capable of producing the biomaterials or bacteria itself can be used as the target substance as the biomaterials.

As the target substance trapping substance, a substance capable of being specifically bound to the above described target substance is utilized. For example, in the case where a combination of the target substance and the target substance trapping substance is enzyme-substrate, antigen-antibody, nucleic acid-nucleic acid, compound—its receptor, and compound—substance having a specific affinity therefor, one of the substances (or compounds) can be used as the target substance trapping substance and the other substance (or compound) can be used as the target substance. The target substance trapping substance can be fixed on the surface of the metal pattern layer by a physical or chemical method.

FIGS. 4 and 15 show the case where an antibody 5 or 204 is used as the target substance trapping substance. When a target substance 4 approaches the antibody 5 or 204 fixed to a metal pattern layer 1 or 201, a complex is formed specifically. Consequently, a dielectric constant, that is, a refractive index on a surface of a detecting device changes.

Although a member in any immunoglobulin class is preferable as for the antibody as a trapping substance used for the present invention, a derivative in an IgG class is more preferable. In addition, an antibody fraction (antibody fragment) fragmented by any method may be used as the antibody as the trapping substance. The antibody fraction means any molecule or complex of an antibody which is shorter than the total length of the above-mentioned antibody or an immunoglobulin. Preferably, the antibody fraction holds a substantial part of the specific binding capability of a full-length antibody. Examples of the antibody fraction may include Fab, Fab', F(ab')2, scFv, Fv, a multispecific multivalent antibody (such as a diabody or a triabody), and an Fd fragment. Since it becomes possible to perform capture nearer to the detecting device when using the antibody fraction, high detection sensitivity can be obtained. In addition, since the multispecific multivalent antibody has specific recognition capacity to each of the detecting device and the target substance, it is possible to fix the trapping substance on a detecting device simply and efficiently.

A complex of an enzyme and a substrate, and a complementary base pair by hybridization of DNA are also examples of the complex, other than the antigen-antibody complex in the present invention. One of substances each of these complexes will be used as a trapping substance of the other. These trapping substances are fixed on a surface of the detecting device by a physical or chemical method.

In order to prevent an unnecessary signal caused by adsorption of impurity in a non-specific adsorption manner, it is also useful to perform coating of a surface of a detecting device. Examples of a coating material may include skim milk, casein, bovine serum albumin, animal serum, phospholipid, polyethylene glycol, and derivatives of these.

In the target substance detecting device according to the present invention, since the refractive index of the underlying layer is equal or close to the refractive index of water contained in the specimen solution, incident light is less liable to be reflected by the underlying layer. As a result, it is possible to extract only a result of interaction of the metal pattern layer with the underlying layer.

In the case of the isolated metal pattern layer, by employing such a constitution that the interval between adjacent metal pattern layers is close to a resonance waveform, it is possible to obtain an interaction of coherent localized plasmon resonance by the influence of a diffraction phenomenon. As a result, a sharper peak waveform can be obtained, so that a spectrum shift can be detected more sensitively. Thus, it is possible to provide a detecting device capable of detecting a trance amount of a target substance in a specimen solution, a target substance detecting method using the detecting device, and a detecting apparatus and kit for the target substance detecting method.

Further, in the case of using the opening-type metal pattern layer, it is possible to further amplify a change in intensity of transmitted light passing through the openings, so that a sensitivity enough to detect the target substance in the specimen solution and a wide dynamic range can be ensured.

In the present invention, the above described various effects can be achieved while maintaining advantages, of detection of a change with time during reaction, intrinsic to the plasmon resonance.

(Detecting Apparatus and Detecting Method)

Figure 8:
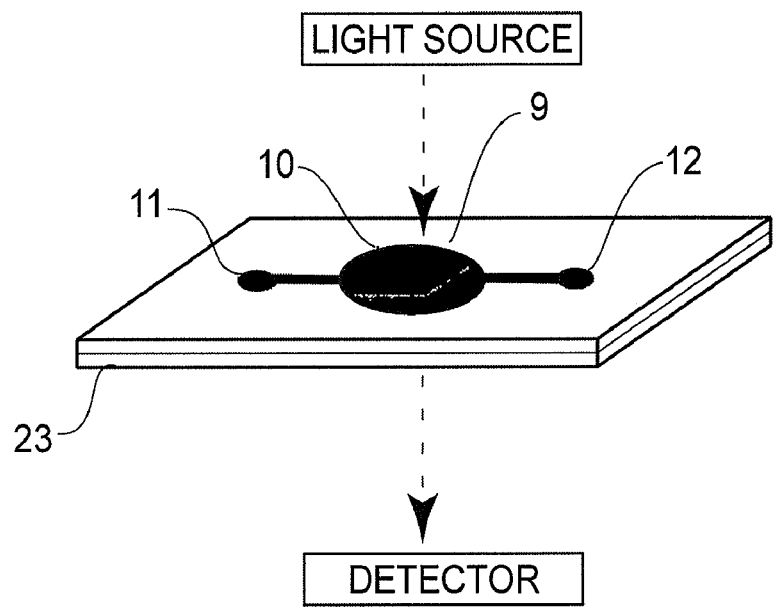
FIG. 8 is a schematic view showing a part of a detecting apparatus in an embodiment of the present invention.

A target substance detecting apparatus using the above-constituted detecting device will be explained. The detecting apparatus according to the present invention includes a holding means for holding the above-constituted detecting device, and a detection means for detecting a signal from a device. An example of the detecting apparatus according to the present invention is shown in FIG. 8.

The detection means includes of an optical detection system constituted by a light source, a spectroscope, and lenses, and a solution sending system which is constituted by an inlet 11 from which a specimen solution flows into the detecting apparatus, a reaction well 9 for moving the specimen to a detecting device 10 on a substrate 23 and reacting it with the device, a path, an outlet 12 from which the specimen flows out of the detecting apparatus, a solution sending mechanism and the like. As the light source, one capable of covering a wavelength region from a visible region to a near infrared region can be used. For the optical measurement, an absorption spectrum, a transmission spectrum, a scattered spectrum, and a reflection spectrum can be employed. Most preferably, a peak wavelength of the absorption spectrum or absorption intensity at its peak is constituted. In the detecting device having the isolated metal pattern layer, when the target substance trapping substance binds a target substance specifically, localized plasmon resonance changes from an unbound state, the peak wavelength of the absorption spectrum is shifted toward a long wavelength, and the absorption intensity increases simultaneously. It is possible to determine an amount of the target substance according to an extent of a shift amount from a calibration curve for the target substance which was prepared in advance. Further, similarly as in the case of transmitted light, it is possible to detect the target substance and determine an amount thereof using reflected light or scattering light. Since the detecting device of the present invention uses the localized plasmon resonance, local electric field enhancement occurs near the isolated metal pattern layer. This phenomenon can be applied also to measuring methods, such as a surface enhanced Raman spectroscopy (SERS) and a surface plasmon fluorescence spectroscopy (SPFS), and determination of an amount of the target substance by these methods is also possible.

It is easy to prepare the reaction well and path with a poly dimethyl siloxane (PDMS) substrate used in a so-called μTAS (Micro Total Analysis Systems) type device. This PDMS substrate will be bonded together with a substrate on which the detecting device is prepared to be used in a shape as shown in FIG. 8. A micro piston pump, a syringe pump, or the like is used as the solution sending mechanism.

Figure 9:
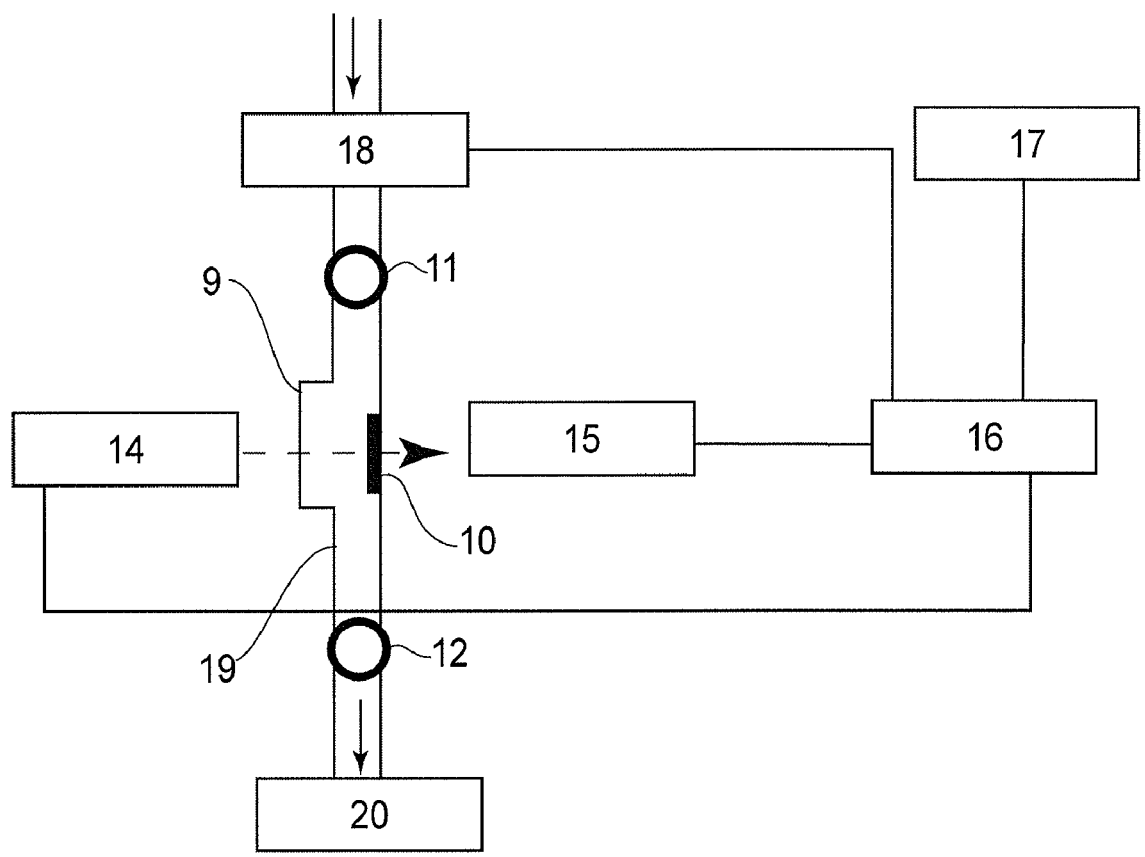
FIG. 9 is a block diagram of a detecting apparatus in an embodiment of the present invention.

Next, a typical usage form is shown in FIG. 9. First, a specimen solution including a target substance is introduced into the reaction well 9, in which the detecting device 10 is disposed, through the path 19 from the inlet 11 by a solution-sending pump 18. Incubation in a fixed time is performed and a transmission spectrum of light from a light source 14 at that time is measured with a spectrophotometer 15. In a central processing unit 16, the measured data is compared with data for calibration having been prepared beforehand, and measurement results, such as a concentration and a reaction rate, are displayed on a display unit 17. If necessary, a phosphate buffer and the like may be introduced from the inlet 11 as cleaning fluid before measurement, and the reaction well 9 may be washed. Here, it is possible to measure a spectral change after a fixed time statically, and also to perform real-time measurement of the change dynamically. In that case, it is possible to acquire a time rate of change and the like as new information. The specimen solution after the measurement is stored in a waster reservoir 20 through an outlet 12.

Figure 14:
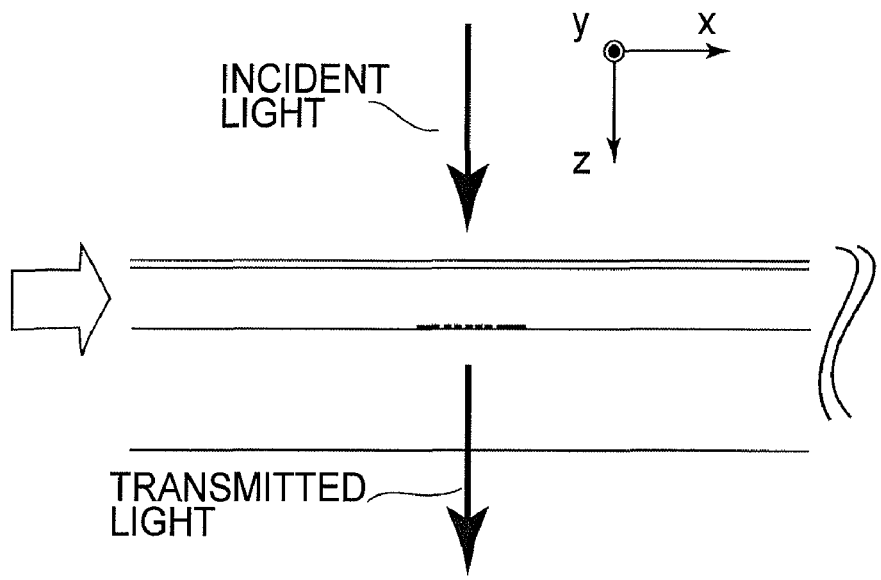
FIGS. 14(A) and 14(B) are schematic views for illustrating an embodiment of the present invention.
Figure 14:
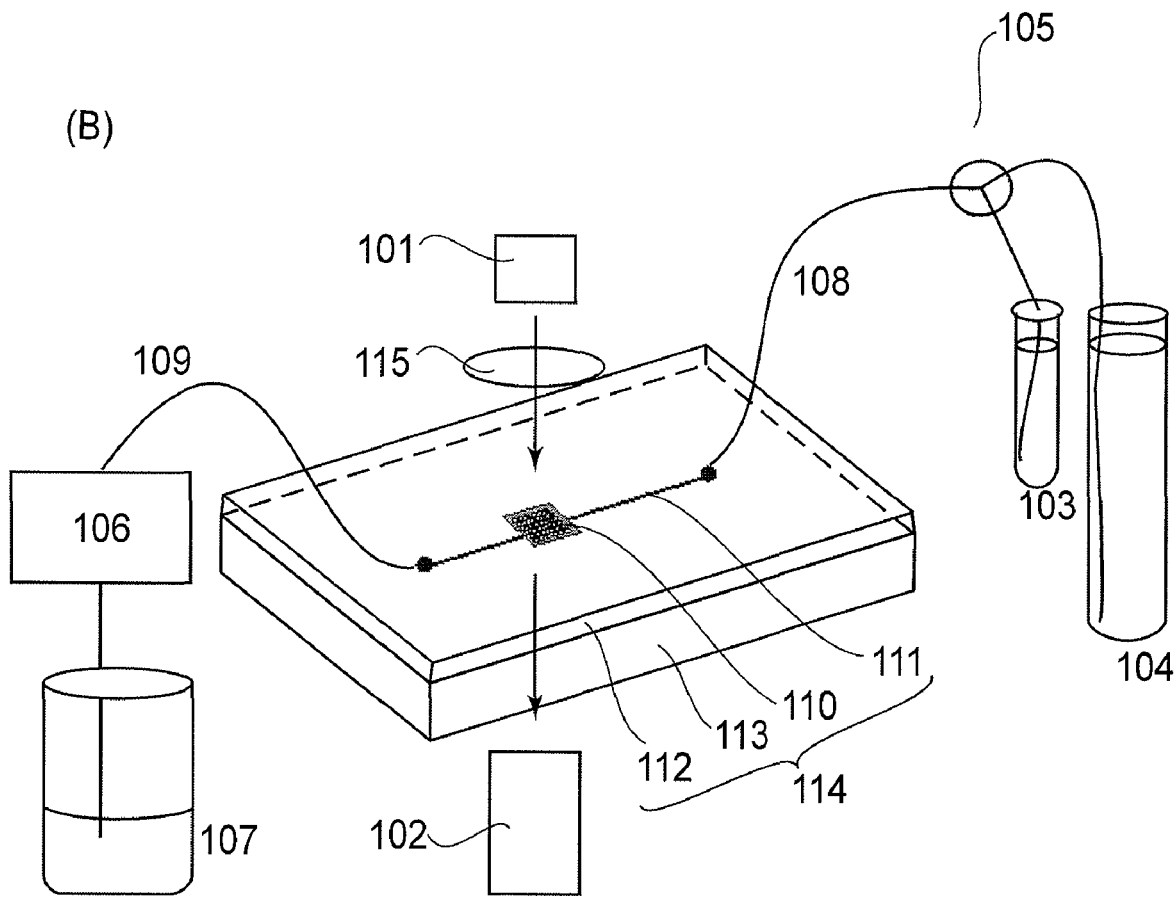

A detecting apparatus of the type wherein transmitted light passing through a detecting device using the opening-type metal pattern layer is measured is shown in FIGS. 14(A) and 14(B), wherein FIG. 14(A) is a sectional view and FIG. 14(B) is a perspective view.

Figure 17:
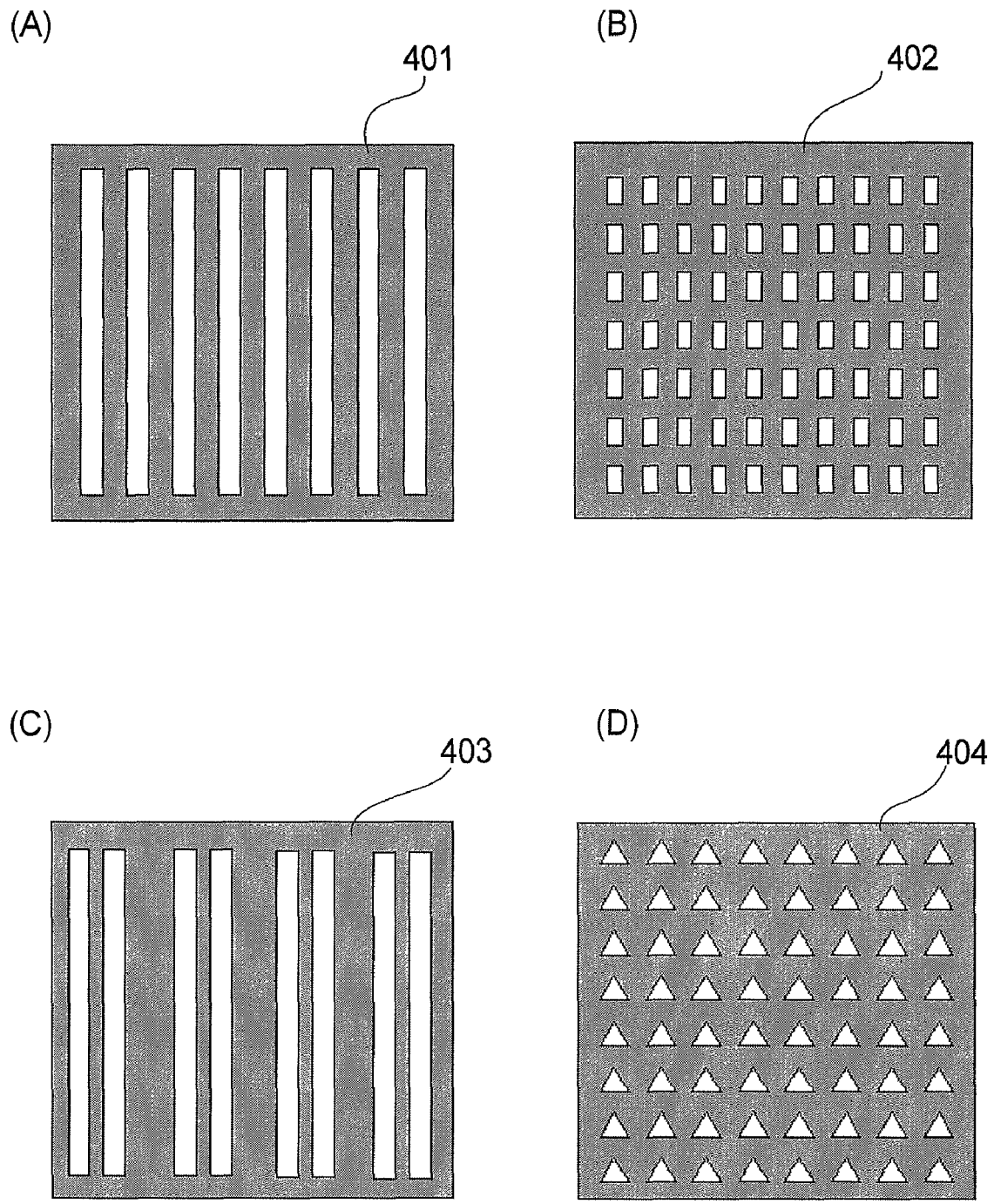
FIGS. 17(A) to 17(D) are schematic views each for illustrating an example of a planar shape of an opening of a metal pattern layer in an embodiment of the present invention.

A light source 101 is not particularly limited so long as it is a stable light source. For example, a halogen lamp may preferably be used. As a light-receiving means, a spectroscopic measurement apparatus having a wavelength resolution of approximately 1 mm may desirably be used. For example, a multichannel detector or a spectrophotometer may preferably be used. A specimen solution reservoir 103 may be a reservoir constituted by a material of less non-specific adsorption of a target substance or a reservoir incorporated into a chip. For example, it is preferable to use an Eppendorf tube subjected to non-specific adsorption prevention coating. A cleaning fluid reservoir 104 is not particularly limited but may preferably be a biochemical glass or plastic tube. A pass switching valve 105 is not particularly limited so long as the fluid tube is switched. For example, a three-way value may preferably be used. As a solution sending means 106, it is possible to appropriately select and use a syringe pump, a tube pump, or a diaphragm pump. As a waste tank 107, in the case of using the syringe pump as the pump, the syringe pump is used as it is. In the case of using the tube pump or the diaphragm pump, it is possible to use a beaker or a bottle as the waste tank. In the case of a small amount of the specimen solution, the specimen solution is not discarded but may also be circulated through a circulating path or a circulating tube. As a solution sending tube 108 and a waste solution tube 109, it is preferable to use a tube formed of a material of the least adsorption of the target substance. As a target substance detecting device 110, the target substance detecting device shown in FIGS. 15 to 17 are appropriately selected and used. As a path 111, a minute path capable of reducing an amount of the specimen solution as small as possible may preferably used. Further, it is preferable that a surface of the path is coated so that an amount of the target substance adsorbed on the surface can be decreased as small as possible. As a cover 112, it is preferable to be constituted by a transparent material capable of forming the path in combination with a substrate 113.

Next, an operation principle of the detecting apparatus using the detecting device having the above described opening-type metal pattern layer will be explained with reference to FIG. 15 and FIGS. 22(A) and 22(B).

In FIG. 15, incident light 205 is caused to enter an array of minute openings 201 in a downward direction (+Z direction). In this case, both of a size and interval of the openings are not more than a wavelength of light for detection, so that a polarized component in X direction of electric field of the incident light 205 interacts with electrons in the metal thin film 201 to generate surface plasmon at an inner surface of the minute openings. The thus penetrated surface plasmon propagates a downward direction (+Z direction) along the inner surface of the minute openings and is converted again into light at a lower end of the minute openings 201, thus passing through in the downward direction (+Z direction).

When the light passes through the plurality of the minute openings 201 through a surface plasmon state, the light is absorbed due to resonance (localized plasmon resonance) with electric multipole generated in the minute openings, so that a spectrum with respect to a change in wavelength of the incident light has a characteristic resonance peak which varies depending no a width or interval of the minute openings. In the detecting device having the opening-type metal pattern layer, the underlying layer having the refractive index equal on close to that of water as a liquid medium of the specimen solution containing the target substance is disposed under the metal thin film (metal pattern layer) having the minute openings, so that the incident light is efficiently converted into transmitted light through plasmon. According to this constitution, a change in integrated intensity of the transmitted light is increased when the target substance is bound to the trapping substance.

Figure 22:
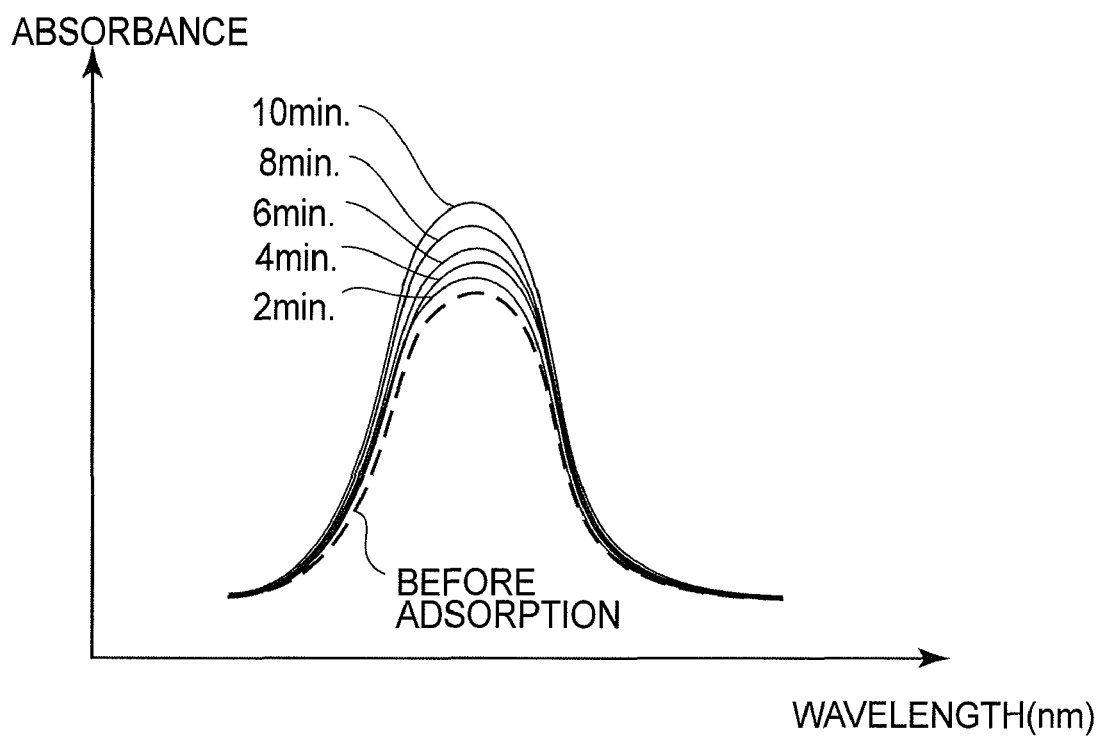
FIGS. 22(A) and 22(B) are graphs each showing an example of transmitted light spectrum in an embodiment of the present invention.
Figure 22:
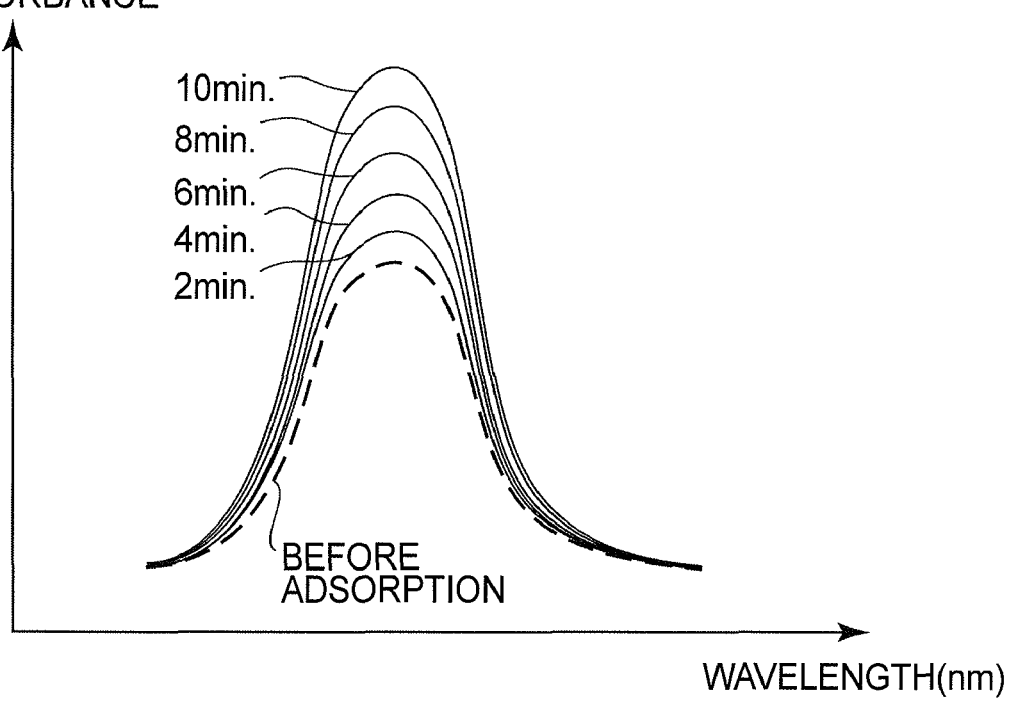
Figure 23:
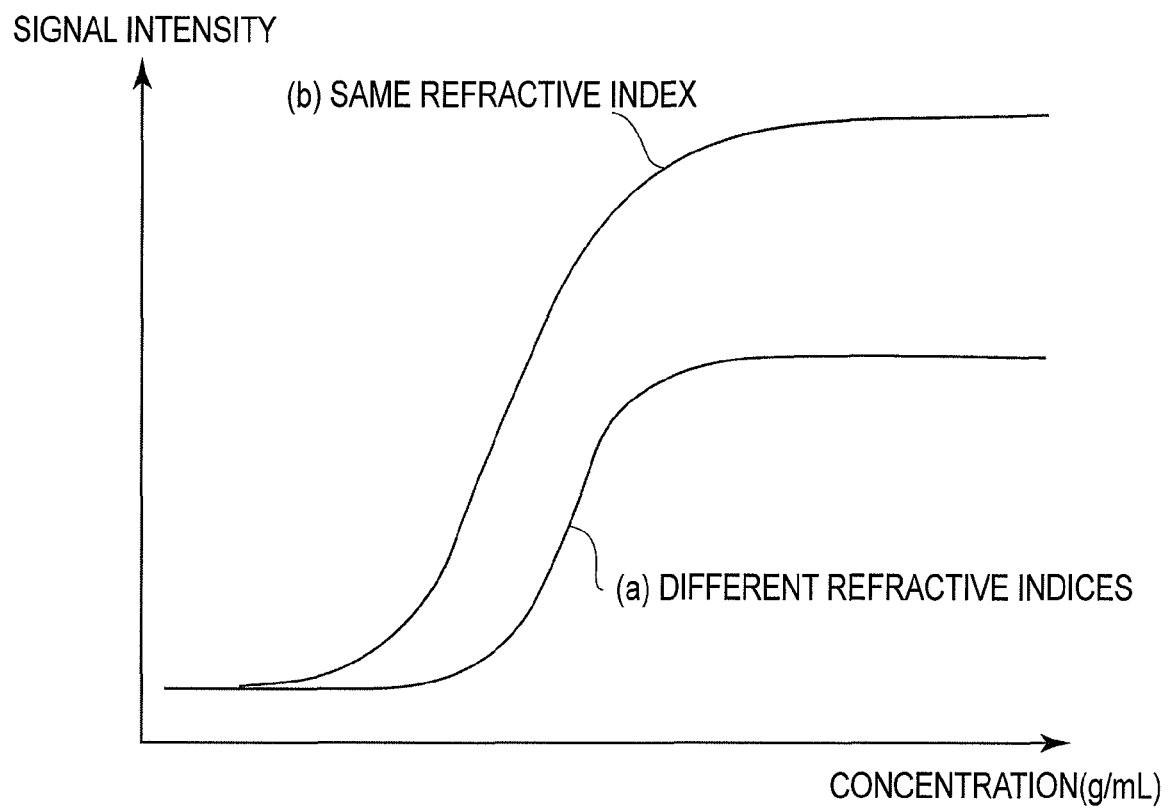
FIG. 23 is a graph showing a change in signal intensity in an embodiment of the present invention.

Examples of a transmitted light intensity spectrum obtained by the detecting apparatus including the detecting device having the above described metal pattern layer are shown in FIGS. 22(A) and 22(B). FIG. 22(A) shows a transmitted light intensity spectrum in the case where a refractive index of an underlying layer is not equal or close to a refractive index of water, and FIG. 22(B) shows a transmitted light intensity spectrum in the case where the refractive index of the underlying layer is equal or close to the refractive index of water. As shown in FIGS. 22(A) and 22(B), it is understood that the integrated intensity change of the transmitted light intensity spectrum is increased in the case where the refractive index of the underlying layer is equal or close to the refractive index of water. FIG. 23 is a graph showing a signal intensity change after specimens having various concentrations are subjected to reaction for a certain time and then are washed with a buffer solution at device surfaces. A curve (a) represents the case where a refractive index of an underlying layer is not equal or close to a refractive index of water, and a curve (b) represents the case where the refractive index of the underlying layer is equal or close to the refractive index of water. As shown in FIG. 23, it can be confirmed that the curve (b) has a lower detection limit and wider dynamic range than those of the curve (a). These curves (a) and (b) show spectra before the target substance reacts with trapping molecules. The detecting index shown in FIG. 15 is caused to contact the specimens containing the target substance to react with the target substance. An integrated intensity of a transmitted light spectrum is gradually increased with an increasing reaction time. A graph showing the change with time of the integrated intensity of FIG. 20. By using a sensor having the above described constitution, it is possible to observe dynamics of the reaction of the target substance with antibody.

A specimen solution for effecting detection of the presence or absence of the target substance or an amount of the target substance is supplied as an aqueous solution constituted by water as a (liquid) solvent. A solute dissolved in the specimen solution principally comprise protein or salts such as phosphates, acetates, borates, trishydrochlorides, chlorides, calcium salts, and magnesium salts. Further, the solve may also contain a cryoprotective agent such as saccharides (e.g., trehalose), glycerol, and ethylene glycol; antiseptics such as sodium azide and thimerosal; protease inhibitors such as PMSF (phenylmethanesulfonyl fluoride) and leupeptin; metal chelators such as EDTA (ethylenediaminetetraacetic acid) (e.g., disodium ethylenediaminetetraacetate); and a reducing agent such as DDT (dithiothreitol).

(Detection Kit)

A kit for detecting the target substance according to the present invention may include those of the following two types (I) and (II):

(I) a target substance detection kit including a substrate for a target substance detecting device and a target substance trapping substance, and (II) a target substance detection kit including a target substance detecting device, a detecting apparatus, a reagent necessary to trap a target substance by the target substance detecting device.

By using the kit of the type (II), it is possible to effect detection of the target substance in the present invention. Further, by using the kit of the type (I), it is possible to provide a new target substance detecting device to a user who has already been in possession of the detecting apparatus or the reagent.

According to the present invention, the detecting device is prepared by disposing the metal pattern layer, to which the target substance trapping substance is bound, on the supporting member through the underlying layer having the refractive index equal or close to that of water, so that it is possible to improve a detection sensitivity by efficiently utilizing incident light for obtaining the plasmon resonance.

The target substance detecting device and the detecting apparatus using the detecting device according to the present invention are suitably usable for detecting of biomaterials (protein, nucleic acid, sugar chain, lipid and the like), allergen, bacteria, virus and the like. Furthermore, the detecting apparatus of the present invention can be applied preferably to a so-called biosensor using an organism origin substance, or its allied substances as a trapping substance component regardless of medical use, industrial use, and home use.

EXAMPLES

The present invention will be further specifically described based on Examples. The present invention is not limited only to the following Examples.

Example 1

Figure 10:
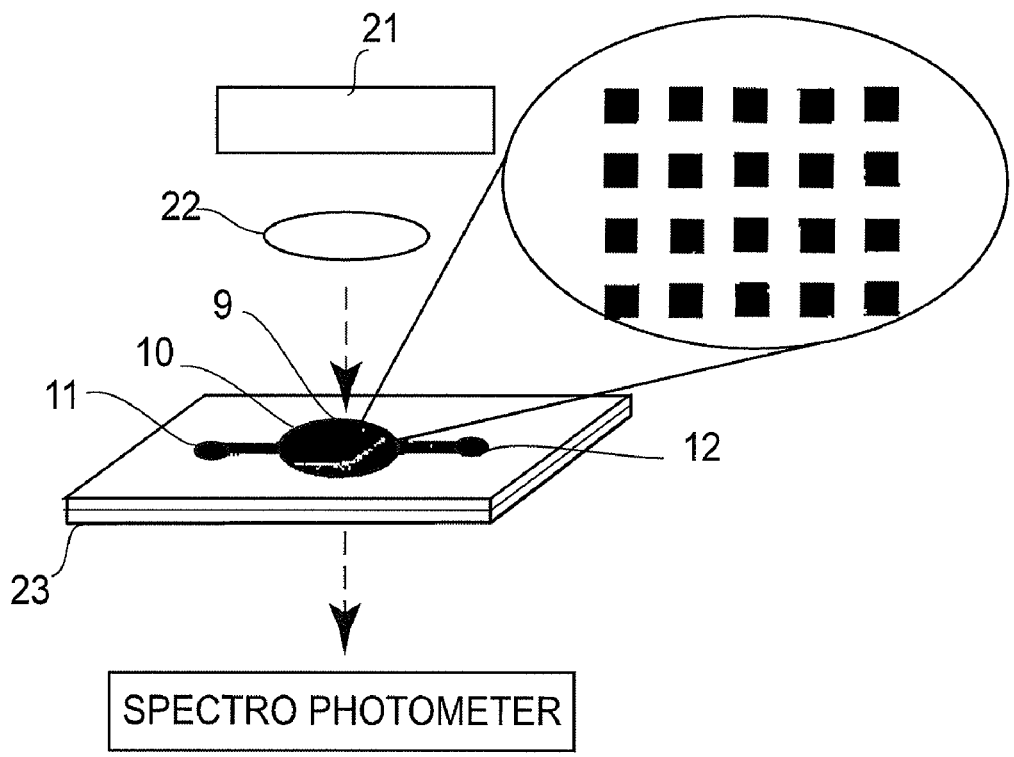
FIG. 10 is a schematic view of a detecting apparatus in Example 1.

FIG. 10 shows a schematic structural view of a detecting apparatus used in this example.

First, on a 625 μm-thick quartz substrate, a 5%-fluorine-containing resin solution (fluorine-containing resin: "CYTOP", solution: "CTL-809M", both mfd. By ASAHI GLASS Co., LTD.) (solvent: "CTL-180", mfd. By ASAHI GLASS Co., LTD.) is spin-coated for 45 seconds at 2500 rpm to obtain a 500 nm-thick layer, followed by drying for 40 minutes at 70° C. and baking for 1 hour at 190° C. to obtain a fluorine-containing resin layer. On the fluorine-containing resin layer, a 20 nm-thick thin film of gold is formed by sputtering.

On the gold thin film, a negative electron beam resist "SAL601", mfd. by Rohm and Haas Company) is formed by spin coating and subjected to patterning by an electron beam lithographic apparatus. The gold thin film is patterned using the resist as a mask to form isolated metal pattern layers. Each metal pattern layer is a square pattern (planar shape) 1200 of 200 nm×200 nm. The isolated metal pattern layers has an interval between adjacent metal pattern layers is 800 nm, and they are regularly disposed in a region of 3 mm×3 mm in an array.

An anti-AFP (α-fetoprotein) antibody as a target substance trapping substance is fixed on a surface of the gold metal pattern layer so as to impart trapping ability to the metal pattern layer surface. The metal pattern layer surface is modified by dropping an ethanol solution of 11-Mercaptoundecanoic acid, which has a thiol group having high affinity for gold, with a spotter or the like. Thereby, a carboxyl group is exposed on the metal pattern layer surface. In the state, an N-Hydroxysulfosuccinimide (mfd. by DOJINDO LABORATORIES) aqueous solution, and a 1-Ethyl-3-[3-dimethylamino]propyl]carbodiimide hydrochloride (mfd. by DOJINDO LABORATORIES) aqueous solution are similarly dropped in a reaction region with a spotter. Thereby, a succinimide group is exposed on the structure surface. Furthermore, by binding streptavidin, the metal pattern layer surface is modified with streptavidin. A biotinylated anti-AFP antibody is fixed to this metal pattern layer.

It is also possible to produce a plurality of regions having a multiplicity of metal pattern layers on the substrate to fix immune bodies which are different from each other, and to take such structure (multisensor structure) that detects different target substances in a specimen solution on the same substrate. In this case, such a structure can be constituted by performing fixing operations similar to the above-mentioned method using different immune bodies in each region.

In the following operations, the AFP concentration in the specimen solution can be measured specifically by using a detecting device 10 prepared above.

A specimen solution which includes AFP which is a target substance is introduced from an inlet 11 in the detecting device 10 for AFP to be made to be caught on the metal pattern layer.

The specimen solution is discharged from an outlet 12, and next, a phosphate buffer is introduced from the inlet 11 for a reaction well 9 to be washed. Finally, a phosphate buffer is filled and an absorption spectrum of the gold metal pattern layer is measured.

Figure 11:
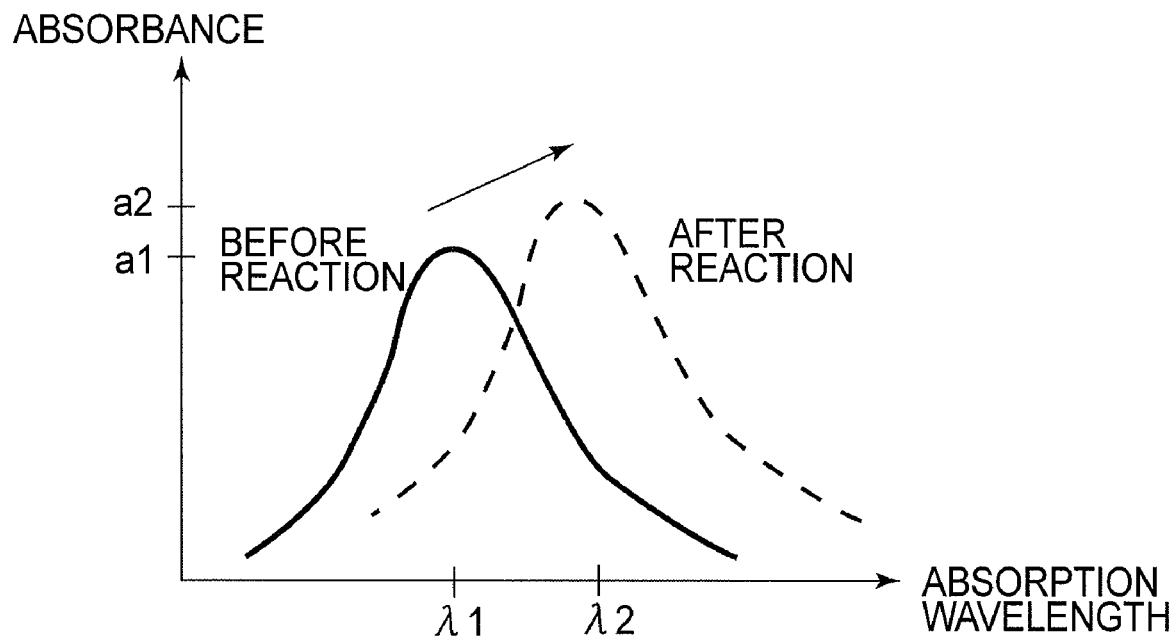
FIG. 11 is a graph showing an example of a change in detection spectrum (absorption spectrum) in Example 1.
Figure 12:
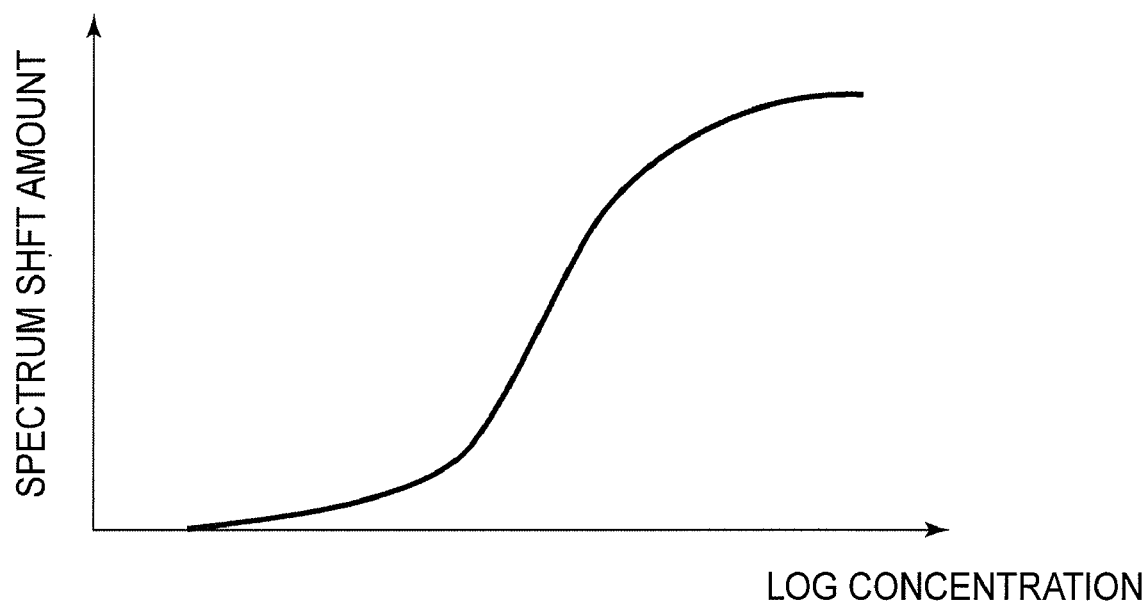
FIG. 12 is a graph showing a calibration curve of a specimen solution in Example 1.

When a curve indicated by a solid line before a reaction is compared with a curve indicated by a dotted line after the reaction, as an example is shown in FIG. 11, the absorption spectrum shifts by a target substance being bound with a surface of the detecting device because of a specific antigen-antibody reaction. Here, correlation between a shift amount of peaks $a_1$ and $a_2$ of an absorbance of the absorption spectrum, or a shift amount of peaks $\lambda_1$ and $\lambda_2$ of an absorption wavelength, and the AFP concentration has been found with known AFP control solutions in advance as a calibration curve in FIG. 12, and thereby, it is possible to find a trace amount of AFP concentration of the specimen solution a concentration of which is unknown.

Example 2

In this example, a substrate having minute projections and recesses is prepared by a mold method using a fluorine-containing resin substrate to provide a detecting device. It is possible to produce the fine projection/recess pattern in a way of producing a common optical disk. An external form of each metal pattern layer is a rectangular pattern of 300 nm×100 nm. A gold thin film has a thickness of 20 nm. The metal pattern layers has an interval between adjacent metal pattern layer is 1400 nm, and they are regularly disposed in a region of 3 mm×3 mm in an array. The gold thin film is formed by a vacuum deposition. Next, then unnecessary gold thin film on a surface is ground to form the metal pattern layers, which have desired layer structure, on a supporting member which also has a function as an underlying layer (FIG. 6(C)).

In order to impart trapping ability to the surface of metal pattern layer, it is processed similarly to Example 1. In this example, an anti-PSA (prostate specific antigen) antibody which is a target substance trapping substance is fixed on the gold metal pattern layer surface.

Similarly to Example 1, when being compared before and after the reaction, the absorption spectrum shifts by a target substance being bound to a surface of the detecting device because of a specific antigen-antibody reaction. Correlation between peak strength of the absorption spectrum, or a shift amount of a peak wavelength, and the PSA concentration has been found with known PSA control solutions beforehand, and thereby, it is possible to find a trace of PSA concentration of the specimen solution a concentration of which is unknown.

Example 3 and Comparative Example 1

In this example (FIG. 3), a shape of metal pattern layers is a rectangular frame-like shape as shown in FIG. 2(E). This metal pattern layer is characterized by having a localized plasmon enhancement effect by the rectangular frame-like shape. Production of a detecting device is made in the same manner as in Example 1 except that a magnesium fluoride thin film formed by vacuum deposition is used in place of the fluorine-containing resin layer. The magnesium fluoride thin film and the gold thin film have thicknesses of 500 nm and 20 nm, respectively. When the metal pattern layer is observed through a scanning electron microscope (SEM), an external form (planar shape) of the metal pattern layer is a square of 200 nm×200 nm, and the rectangular frame-like portion has a line width of 50 nm. Depending on a degree of resolution of a rendering process, a shape of corners cannot be necessarily produced at right angles but there is no problem in terms of function. The metal pattern layers have an interval between adjacent metal pattern layers of 1350 nm and are regularly disposed in a region of 3 mm×3 mm in an array.

In this example in which the metal pattern layers are disposed on the magnesium fluoride thin film, compared with the case where the magnesium fluoride thin film is not used (Comparative Example 1), A half-value width of an absorption spectrum of localized plasmon resonance is decreased by approximately 20-40%.

Example 4

In this example, a shape of metal pattern layers is formed as a structure having a cross-like portion as shown in FIG. 2(I). This structure is characterized by having a localized plasmon resonance enhancement effect by the cross-like portion. The metal pattern layers are formed on a 625 μm-thick quartz substrate in the following manner. First, on the quartz substrate, a 50 nm-thick lithium fluoride thin film is formed. Thereafter, I the same manner as in Example 1, formation of a 20 nm-thick gold thin film by sputtering, and patterning and etching of the resultant structure with an electron beam lithographic process are successively performed to obtain the metal pattern layers. When the metal pattern layers are observed through a scanning electron microscope (SEM), an external form (planar shape) in a span of 500 nm of the metal pattern layers is a square of 200 nm×200 nm, and the cross-like portion has a line width of 50 nm. Depending on a degree of resolution of a rendering process, a shape of crossing cannot be necessarily produced at right angles but there is no problem in terms of function. The metal pattern layers have an interval between adjacent metal pattern layers of 1250 nm and are regularly disposed in a region of 3 mm×3 mm in an array.

The detecting device of this example can also be used as a biosensor similarly as in the above described Examples.

Example 5

Target Substance Detecting Device

A target substance detecting device in this example will be described with reference to FIG. 15.

As a supporting member 203, a glass plate is used. On the supporting member 203, a 200 nm-thick layer of $MgF_2$ is formed as an underlying layer 202 by vacuum deposition. On the underlying layer 202, a 200 nm-thick metal pattern layer 201 is formed by vacuum deposition. On the metal pattern layer 201, a positive electron beam resist (ZEP520) is spin-coated, followed by patterning by electron beam lithography. The metal pattern layer 201 is etched using the resist pattern as a mask so that a plurality of rectangular portions each having a size of 300 nm×50 nm is arranged in an array at an interval of 1000 nm. As a target substance trapping substance, antibody is used.

<Target Substance Detecting Apparatus>

A target substance detecting apparatus in this example will be described with reference to FIGS. 14(A) and 14(B), wherein FIG. 14(A) is a sectional view and FIG. 14(B) is a perspective view.

The target detecting apparatus includes a halogen lamp as a light source 101, a multichannel detector (mfd. by Hamamatsu Photonics K.K.) as a spectrosocope 102, an Eppendorf tube as a specimen solution reservoir 103, a biochemical glass bottle as a cleaning liquid reservoir 104, a three-way valve (mfd. by GL Sciences Inc.) as a path switching valve 105, a syringe pump "KDS200", mfd. by KD Scientific Inc.) as a solution sending means 106, a syringe as a waste solution tank 107, a Teflon tube as a solution sending tube 108, and a Teflon tube as a waste solution tube 109.

As a target substance detecting device 110, the above prepared target substrate detecting device described with reference to FIG. 15 is used. A (flow) path 111 is formed on a cover (PDMS substrate) 112 in a width of 1 mm, a thickness (depth) of 100 μm, and a length of 40 mm. As a substrate 113, a quartz glass substrate is used. Further, as a collimating lens, a planoconvex lens (mfd. by SIGMA KOKI Co., Ltd.) having a size of 20 mm×40 mm is used. The target substance detecting device 110, the path 111, the cover 112, and the substrate 113 constitute a target substance detection chip 114.

<Measurement of Target Substance>

In the detecting apparatus shown in FIGS. 14(A) and 14(B), the target substance detecting device 110 on which an anti-PSA antibody is fixed is set in the detecting apparatus and the following protocol (procedure) is performed. The fixation of the antibody on the surface of metal pattern layer can be effected in the same manner as in Example 1.

(1) A direction of the three-way valve is switched to a cleaning liquid side, so that a buffer solution adjusted to have a pH of 7.4 is caused to flow for 10 minutes at a flow rate of 0.1 (ml/min.) to sufficiently wash the target substance detecting device.

(2) The valve direction is switched to a specimen solution side, so that a specimen solution is caused to flow for 10 minutes at a flow rate of 0.1 (ml/min.) to cause an antigen-antibody reaction.

(3) A reflection spectrum is measured at regular time intervals while sending the specimen solution.

(4) The valve direction is switched again to the cleaning liquid side, so that the buffer solution is caused to flow for 10 minutes at a flow rate of 0.1 (ml/min.) to wash away the antigen which has been adsorbed nonspecifically.

Figure 18:
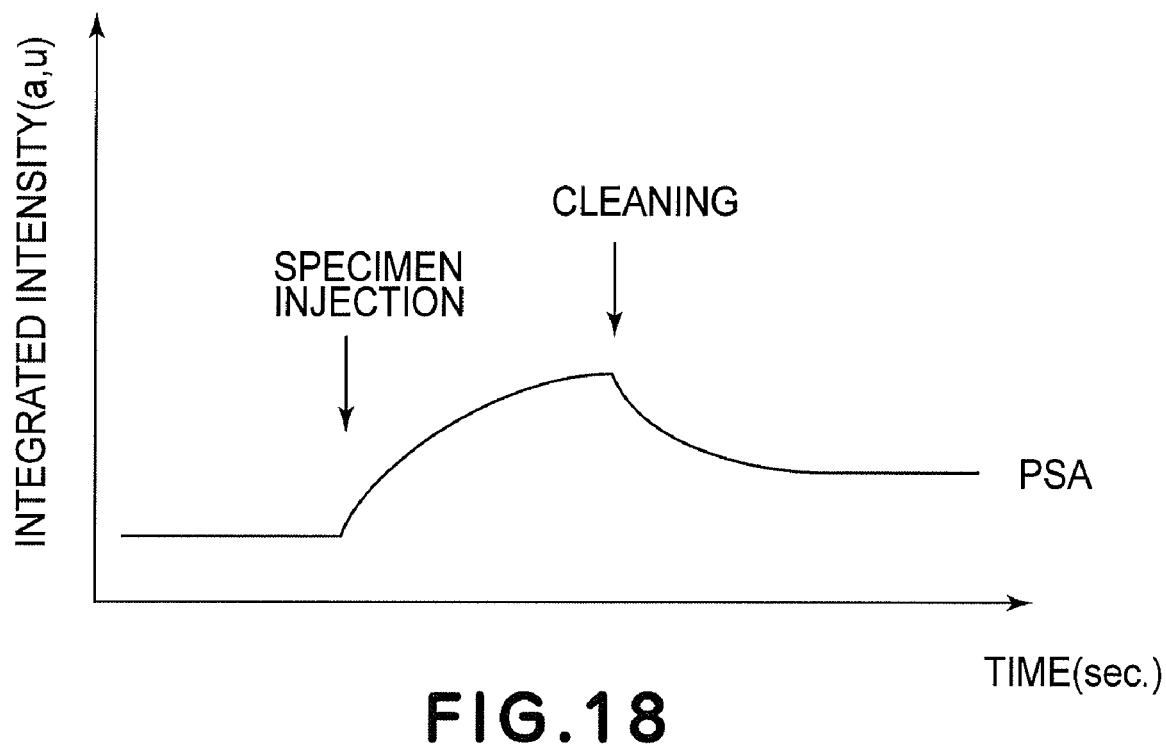
FIG. 18 is a graph showing a time course of an antigen-antibody reaction in Example 5.

By the above described protocol, it is possible to obtain spectra for each reaction time similar to those shown in FIGS. 22(A) and 22(B). These spectra are integrated by a plotting and graphing software to obtain integrated values for respective reaction times, to that it is possible to obtain a time course of the antigen-antibody reaction as shown in FIG. 18.

Example 6

In this example, four target substrate detecting devices on which mutually different types of antibodies are fixed are disposed in series in a form of a chip. Each of the four target substance detecting devices is prepared in the same manner as in Example 5, in which the target substance detecting device as shown in FIG. 15 is prepared, except that predetermined antibodies (different in type) are used.

<Target Substance Detecting Apparatus>

A target substance detecting apparatus in this example will be described with reference to FIG. 19 which is a perspective view.

The target detecting apparatus includes a halogen lamp as a light source 61, a multichannel detector capable of effecting four-channel simultaneous measurement as a spectroscope 602, an Eppendorf tube as a specimen solution reservoir 603, a biochemical glass bottle as a cleaning liquid reservoir 604, a three-way valve (mfd. by GL Sciences Inc.) as a path switching valve 605, a syringe pump "KDS200", mfd. by KD Scientific Inc.) as a pump 606, a syringe as a waste solution tank 607, a Teflon tube as a solution sending tube 608, and a Teflon tube as a waste solution tube 609.

As a target substance detecting device 610, the above prepared chip including the four target substrate detecting devices described with reference to FIG. 15, disposed in series is used. A (flow) path 611 is formed on a cover (PDMS substrate) 612 in a width of 1 mm, a thickness (depth) of 100 μm, and a length of 40 mm. As a substrate 613, a quartz glass substrate is used. Further, as a collimating lens, a planoconvex lens (mfd. by SIGMA KOKI Co., Ltd.) having a size of 20 mm×40 mm is used. An optical fiber 616 is not particularly limited so long as an amount of light from the light source 601 is sufficiently ensured in each wavelength range. In this example, an optical fiber for visible wavelength range may preferably be used. The detecting apparatus further includes a target substance detection chip 614 and couplers 615.

<Measurement of Target Substance>

Figure 19:
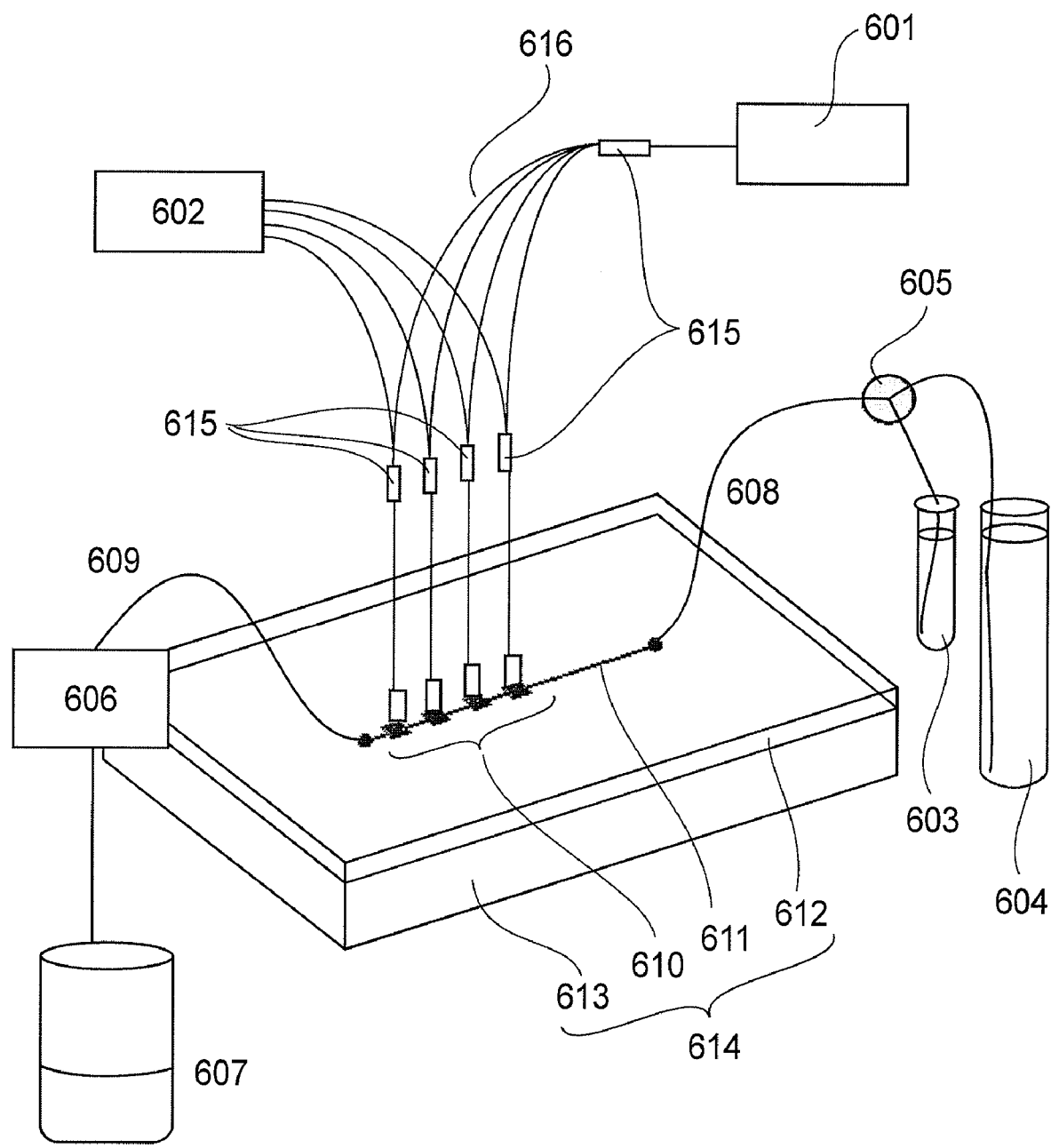
FIGS. 19 and 21 are schematic views for illustrating target substance measuring apparatuses in Examples 6 and 7, respectively.

In the detecting apparatus shown in FIG. 19, each of the four target substance detecting devices 610 on which an anti-CEA (carcinoembryonic antigen) antibody an anti-AFA (alpha-fetoprotein) antibody, an anti-PSA antibody, and an anti-PAP (prostatic acid phosphatase) antibody are fixed, respectively, is set in the detecting apparatus and the following protocol (procedure) is performed.

(1) A direction of the three-way valve is switched to a cleaning liquid side, so that a buffer solution adjusted to have a pH of 7.4 is caused to flow for 10 minutes at a flow rate of 0.1 (ml/min.) to sufficiently wash the target substance detecting device.

(2) The valve direction is switched to a specimen solution side, so that a specimen solution is caused to flow for 10 minutes at a flow rate of 0.1 (ml/min.) to cause an antigen-antibody reaction.

(3) A reflection spectrum is measured at regular time intervals while sending the specimen solution.

(4) The valve direction is switched again to the cleaning liquid side, so that the buffer solution is caused to flow for 10 minutes at a flow rate of 0.1 (ml/min.) to wash away the antigen which has been adsorbed nonspecifically.

Figure 20:
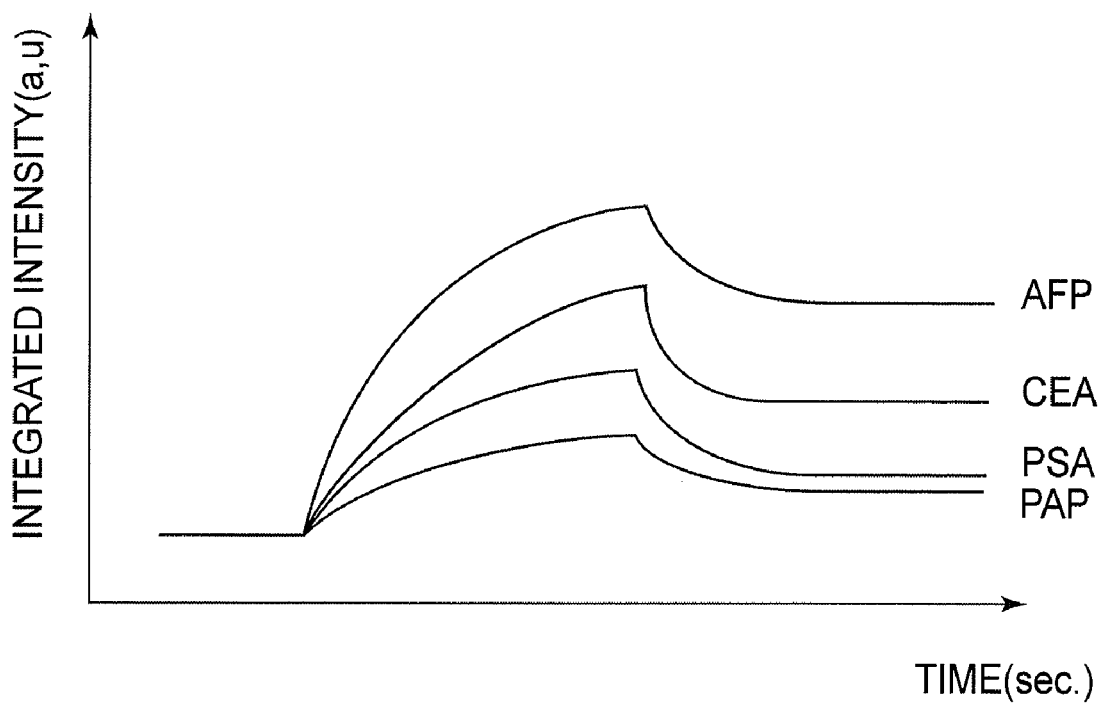
FIG. 20 is a graph showing a change with time in integrated intensity of transmitted light spectrum in an embodiment of the present invention.

By the above described protocol, it is possible to obtain spectra for each reaction field as shown in FIGS. 22(A) and 22(B). These spectra are subjected to function fitting by plotting and graphing software to obtain peak values for respective reaction times, to that it is possible to effect measurement of reaction kinetics for respective marker proteins as shown in FIG. 20.

As described above, by measuring reaction profiles of a plurality of disease marker proteins and their antibodies, it is possible to investigate a disease factor with high accuracy through measurement of a single protein.

Example 7

In this example, four target substrate detecting devices on which mutually different types of antibodies are fixed are disposed in series in a form of a chip. Each of the four target substance detecting devices is prepared in the same manner as in Example 4, in which the target substance detecting device as shown in FIG. 15 is prepared, except that predetermined antibodies (different in type) are used.

<Target Substance Detecting Apparatus>

A target substance detecting apparatus in this example will be described with reference to FIG. 21 which is a perspective view.

The target detecting apparatus includes a halogen lamp as a light source 801, a multichannel detector capable of effecting four-channel simultaneous measurement as a spectroscope 802, an Eppendorf tube as a specimen solution reservoir 803, a biochemical glass bottle as a cleaning liquid reservoir 804, a three-way valve (mfd. by GL Sciences Inc.) as a path switching valves 805 and 817, a syringe pump "KDS200", mfd. by KD Scientific Inc.) as a pump 806, a beaker as a waste solution tank 807, a Teflon tube as a solution sending tube 808, and a Teflon tube as a waste solution tube 809.

As a target substance detecting device 810, the above prepared chip including the four target substrate detecting devices described with reference to FIG. 15, disposed in series is used. A (flow) path 811 is formed on a cover (PDMS substrate) 612 in a width of 1 mm, a thickness (depth) of 100 µm, and a length of 40 mm. As a substrate 813, a quartz glass substrate is used. Further, as a collimating lens, a planoconvex lens (mfd. by SIGMA KOKI Co., Ltd.) having a size of 20 mm×40 mm is used. As a circulating tube 818, a Teflon tube is used. The detecting apparatus further includes a target substance detection chip 814, couplers 815, and an optical fiber 816.

<Measurement of Target Substance>

Figure 21:
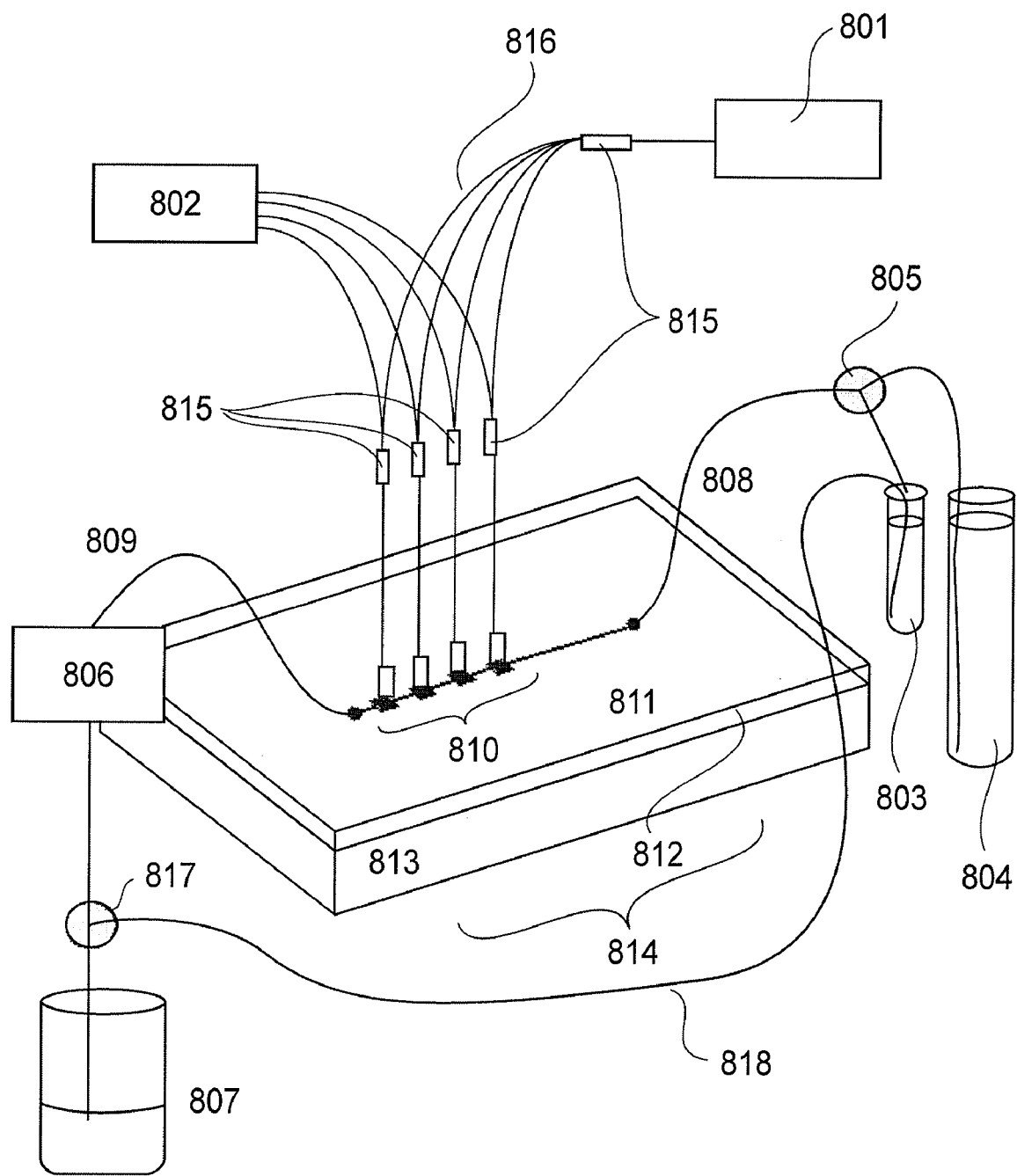

In the detecting apparatus shown in FIG. 21, each of the four target substance detecting devices 610 on which an anti-CEA (carcinoembryonic antigen) antibody an anti-AFA (alpha-fetoprotein) antibody, an anti-PSA antibody, and an anti-PAP (prostatic acid phosphatase) antibody are fixed, respectively, is set in the detecting apparatus and the following protocol (procedure) is performed.

(1) The valve 805 is set to a cleaning liquid side and the valve 817 is set to a waste solution tank side, so that a buffer solution adjusted to have a pH of 7.4 is caused to flow for 10 minutes at a flow rate of 0.1 (ml/min.) to sufficiently wash the target substance detecting device.

(2) The valve 805 is set to a specimen solution side and the valve 817 is set to a circulating tube side, so that a specimen solution is caused to flow for 10 minutes at a flow rate of 0.1 (ml/min.) to cause an antigen-antibody reaction.

(3) A reflection spectrum is measured at regular time intervals while sending the specimen solution.

(4) The valve direction is switched again to the cleaning liquid side, so that the buffer solution is caused to flow for 10 minutes at a flow rate of 0.1 (ml/min.) to wash away the antigen which has been adsorbed nonspecifically.

By the above described protocol, it is possible to obtain spectra for each reaction field as shown in FIGS. 22(A) and 22(B). These spectra are subjected to function fitting by plotting and graphing software to obtain peak values for respective reaction times, to that it is possible to effect measurement of reaction kinetics for respective marker proteins as shown in FIG. 20.

As described above, by measuring reaction profiles of a plurality of disease marker proteins and their antibodies, it is possible to investigate a disease factor with high accuracy through measurement of a single protein.

Example 8

A detecting apparatus as shown in FIG. 10 is constituted in the same manner as in Example 1 except that the target substance trapping substance is changed to a bispecific antibody (diabody) described in Japanese Laid-Open Patent Application No. 2005-312446.

This diabody is used for imparting trapping ability to the surface of the metal pattern layer and has specific affinity for two substances of gold, which is a material for the metal pattern layer of the detecting device, and HEL (hen egg white lysozyme), which is a target substance. The thus prepared diabody is added in a detecting device portion with a phosphate buffer, and is washed with a buffer solution and is used, after incubation for about 30 minutes. According to the method, using the diabody, of this example, in comparison with a chemically fixing method, it is possible to perform fixing without impairing affinity, and in consequence, it is possible to reduce an amount of trapping substance required for fixing it on the detecting device.

Next, by the following operations using the detecting apparatus, the HEL concentration in a specimen can be measured specifically.

(1) A specimen which includes HEL which is a target substance is introduced from an inlet 11 in the produced device for HEL to be made caught on the structure.

(2) The specimen is discharged, and a phosphate buffer is introduced from the inlet 11 for an interior of a reaction well 9 to be washed.

(3) Finally, a phosphate buffer is filled and an absorption spectrum of the gold metal pattern layer is measured.

When an absorption spectrum is compared before and after the reaction, the absorption spectrum shifts by the target substance being bound with a surface of the detecting device because of a specific antigen-antibody reaction, as shown in FIG. 23 as an example. Here, correlation between peak strength of the absorption spectrum, or a shift amount of a peak wavelength, and the HEL concentration has been found with known HEL control solutions in advance, and hence, it is possible to find a trace amount of HEL concentration of the specimen a concentration of which is unknown.

INDUSTRIAL APPLICABILITY

As described hereinabove, according to the present invention, it is possible to provide a target substance detecting device capable of improving a detection sensitivity in detection of a target substance by utilizing localized plasmon resonance and a substrate for preparing the target substance detecting device.

It is also possible to provide a target substance detecting apparatus and target substance detecting method which employ the target substance detecting device. It is further possible to provide a kit for the target substance detecting method.

While the invention has been described with reference to the structures disclosed herein, it is not confirmed to the details set forth, and this application is intended to cover such modifications or changes as may come within the purposes of the improvements or the scope of the following claims.

The invention claimed is:

1. A substrate for forming a target substance detecting device, comprising:
   a supporting member;
   an underlying layer disposed on a surface of the supporting member; and
   a metal pattern layer, disposed on a surface of the underlying layer, for being bound to a target substance trapping substance capable of trapping a target substance in a specimen solution at least containing water as a liquid medium to detect the target substance by utilizing plasmon resonance,
   wherein the underlying layer has a refractive index $n_b$ satisfying the following relationship:

$$0.90\, n_a \leq n_b \leq 1.05\, n_a,$$

wherein na represents a refractive index of water, and wherein the metal pattern layer comprises a plurality of metal patterns formed in isolation on the surface of the underlying layer.

2. A substrate according to claim 1, wherein the refractive index nb is in a range of from 1.20 to 1.40.

3. A substrate according to claim 1, wherein the underlying layer comprises a fluorine-containing material.

4. A substrate according to claim 3, wherein the fluorine-containing material is a fluorine-containing resin.

5. A substrate according to claim 3, wherein the fluorine-containing material is magnesium fluoride or lithium fluoride.

6. A substrate according to claim 1, wherein the plurality of metal patterns has an interval, between adjacent metal patterns, in a range of from 400 nm to 1500 nm.

7. A target substance detecting device comprising:
a substrate according to claim 1; and
a target substance trapping substance,
wherein the metal pattern layer of the substrate is bound to the target substance trapping substance.

8. A device according to claim 7, wherein the target substance trapping substance is an antibody.

9. A device according to claim 8, wherein the antibody is an antibody fraction.

10. A device according to claim 9, wherein the antibody fraction is a multispecific multivalent antibody.

11. A target substance detecting apparatus for detecting a target substance in a specimen solution, comprising:
target substance detecting device according to claim 7,
specimen solution supplying means for supplying the specimen solution to the target substance detecting device; and
detecting means for detecting trapping of the target substance by the target substance trapping substance of the target substance detecting device.

12. An apparatus according to claim 11, wherein the detecting means is optically detecting means for optically detecting the trapping of the target substance by the target substance trapping substance.

13. An apparatus according to claim 12, wherein the optically detecting means detects transmitted light, scattering light, a reflected light from the target substance detecting device.

14. An apparatus according to claim 11, wherein the target substance detecting device is disposed in a flow path.

15. A target substance detecting method for detecting presence or absence of a target substance in a specimen solution at least containing water as a liquid medium or for detecting an amount of the target substance, comprising the steps of:
bringing a target substance detecting device according to claim 7 into contact with the target substance; and
detecting trapping the target substance on the target substance detecting device when the specimen solution contains the target substance.

16. A target substance detection kit for detecting presence or absence of a target substance in a specimen solution or an amount of the target substance, comprising:
a target substance detecting device according to claim 7; and
a reagent necessary for trapping of the target substance by the target substance detecting device.

* * * * *